United States Patent
Antel et al.

(10) Patent No.: US 7,592,344 B2
(45) Date of Patent: Sep. 22, 2009

(54) NK1 AND NK2-ANTAGONISTS AND COMPOSITIONS AND METHODS OF USING THE SAME

(75) Inventors: Jochen Antel, Muender (DE); Daniel Jasserand, Hannover (DE); Uwe Schoen, Burgdorf (DE); Michael Firnges, Barsinghausen (DE); Holger Sann, Hannover (DE); Reinhard Brueckner, Hannover (DE); Dania Reiche, Adelheidsdorf (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 1 day.

(21) Appl. No.: 11/606,337

(22) Filed: Nov. 30, 2006

(65) Prior Publication Data

US 2007/0149537 A1 Jun. 28, 2007

Related U.S. Application Data

(60) Provisional application No. 60/740,815, filed on Nov. 30, 2005.

(51) Int. Cl.
*A61K 31/496* (2006.01)
(52) U.S. Cl. ............... 514/252.12; 514/252.13; 514/253.01; 514/254.1; 514/254.11; 544/360; 544/376; 544/377; 544/379; 544/400
(58) Field of Classification Search ........... 544/360, 544/374, 379, 400, 402, 403, 377, 376; 514/252.12, 514/252.13, 253.01, 254.1, 254.11
See application file for complete search history.

(56) References Cited

U.S. PATENT DOCUMENTS

| | | | |
|---|---|---|---|
| 5,236,921 A | 8/1993 | Emonds-Ai et al. | |
| 5,317,020 A | 5/1994 | Emonds-Alt et al. | |
| 5,607,936 A | 3/1997 | Chiang et al. | |
| 6,232,467 B1 | 5/2001 | Petasis et al. | |
| 6,602,817 B1 | 8/2003 | Petasis | |
| 6,770,649 B2 | 8/2004 | Jasserand et al. | |
| 2006/0167008 A1 | 7/2006 | Janssens et al. | |

FOREIGN PATENT DOCUMENTS

| | | |
|---|---|---|
| EP | 0 428 434 A2 | 5/1991 |
| EP | 0 474 561 B1 | 3/1992 |
| EP | 1 293 506 A1 | 3/2003 |
| WO | WO 96/10568 A1 | 4/1996 |
| WO | WO 98/00398 A1 | 1/1998 |
| WO | WO 00/24510 A1 | 5/2000 |
| WO | WO 2004/033428 A1 | 4/2004 |

OTHER PUBLICATIONS

Norma P. Gerard et al., "The Human Neurokinin A (Substance K) Receptor", The Journal of Biological Chemistry, vol. 265, No. 3, Nov. 25, 1990, pp. 20455-20462.
Nicos A. Petasis et al., "Highly Stereocontrolled One-Step Synthesis of anti-β-Amino Alcohols from Organoboronic Acids, Amines, and α-HydroxyAldehydes", J. Am. Chem. Soc., 1998, vol. 20, pp. 11798-11799.
International Search Report dated Feb. 6, 2007 and PCT/ISA/237 (Twelve (12) Pages).

*Primary Examiner*—Bernard Dentz
*Assistant Examiner*—David E Gallis
(74) *Attorney, Agent, or Firm*—Crowell & Moring LLP

(57) ABSTRACT

3-cyanonaphthalene-1-carboxylic acid perhydroxyalkylmethyl-piperazine compounds of formula I

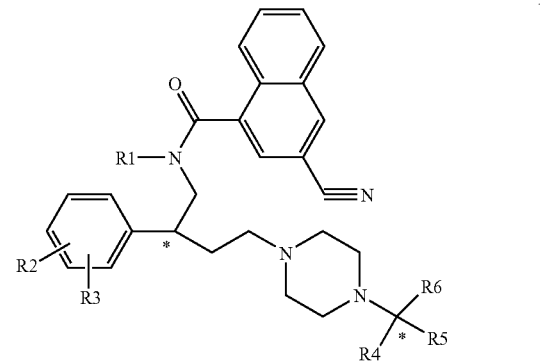

which are antagonistic to tachykinin receptors, pharmaceutical compositions containing such compounds, methods of using such compounds for the treatment and/or inhibition of various diseases and disorders, processes for preparing such piperazine compounds, and intermediate products of these processes.

16 Claims, No Drawings

NK1 AND NK2-ANTAGONISTS AND COMPOSITIONS AND METHODS OF USING THE SAME

FIELD OF THE INVENTION

The present invention relates to novel 3-cyano-naphthalene-1-carboxylic acid perhydroxyalkylmethyl-piperazine compounds which are antagonistic to tachykinin receptors, to pharmaceutical compositions comprising these compounds, and to methods of using the same. Furthermore, the invention relates to processes for the preparation of the novel piperazine compounds and to intermediate products of these processes.

BACKGROUND OF THE INVENTION

The tachykinins include the naturally-occurring neuropeptides substance P, neurokinin A and neurokinin B. The tachykinins act as agonists of receptors occurring in larger mammals and humans, such as the neurokinin (NK) 1, 2 and 3 receptors. Artificially prepared compounds which are antagonistic to tachykinin receptors are usually classified according to their relative ability to bind to one or more of the aforementioned three receptor subtypes. In the physiological process the tachykinins play an important part in the transmission of pain, emesis, neurogenic inflammations, bladder inflammation, inflammatory joint diseases or asthmatic complaints.

Piperazine derivatives which act as antagonists to the $NK_1$ receptor are known from U.S. Patent Publication No. 2004/03428 (=WO 2004/033428). Piperazine derivatives which act as antagonists to the $NK_2$ receptor are known from U.S. Pat. No. 6,770,649 (=EP 1,293,506). Piperazine derivatives which can act as antagonists to tachykinin receptors are known from U.S. Pat. No. 5,607,936 (=WO 96/10568).

It would be desirable to have new active substances having properties antagonistic to tachykinin receptors $NK_1$ and $NK_2$, which are suitable in particular for the treatment and/or inhibition of respiratory diseases, in particular asthma, bronchitis, cough, and rhinitis; skin diseases, in particular inflammatory skin reactions, allergic skin reactions, and psoriasis; arthropathic diseases, in particular arthritis, vasculitides and systemic lupus erythematosus; functional or inflammatory disorders in the gastrointestinal tract, in particular pseudomembranous colitis and diarrhea; bleb diseases such as cystitis and interstitial cystitis; and migraine.

SUMMARY OF THE INVENTION

It has now been surprisingly found that a group of novel 3-cyano-naphthalene-1-carboxylic acid perhydroxyalkylmethyl-piperazine compounds exhibits excellent antagonism to tachykinin receptors, in particular to and $NK_1$- and $NK_2$ receptors. These compounds exhibit a marked action component directed at the peripheral region. Accordingly, the group of compounds according to the invention appears particularly suitable for the treatment of peripheral disorders in which tachykinins, in particular neurokinin A, participate as transfer agents, for example for the treatment and/or prophylaxis of respiratory diseases, in particular asthma, bronchitis, cough, and rhinitis; skin diseases, in particular inflammatory skin reactions, allergic skin reactions, and psoriasis; arthropathy diseases, in particular arthritis, vasculitides and systemic lupus erythematosus; functional or inflammatory disorders in the gastrointestinal tract, in particular pseudomembranous colitis and diarrhea; bleb diseases such as cystitis and interstitial cystitis; and migraine.

In one embodiment, the present invention provides novel 3-cyano-naphthalene-1-carboxylic acid perhydroxyalkylmethyl-piperazine compounds of the formula I,

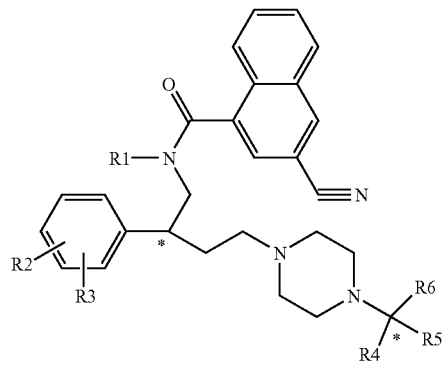

wherein
R1 is selected from the group consisting of hydrogen and $C_1$ to $C_4$ alkyl;
R2 is halogen;
R3 is halogen;
R4 is selected from the group consisting of 2-furanyl, 3-furanyl, 2-thiophene, 3-thiophene, phenyl, benzyl, 2-benzofuranyl, 3-benzofuranyl, 5-chloro-2-thiophene, 4-methylphenyl, 3,4-methylenedioxyphenyl, 2-methoxyphenyl, 4-methoxyphenyl, 2-pyridinyl, 3-pyridinyl, 1-benzo[c]thiophene, 4-benzo[c]thiophene, 5-benzo[c]thiophene, 2-benzo[b]thiophene, 3-benzo[b]thiophene, 4-benzo[b]thiophene, 5-benzo[b]thiophene, 6-benzo[b]thiophene, 7-benzo[b]thiophene, 1-benzo[1,3]dioxole, 4-benzo[1,3]dioxole, and 5-benzo[1,3]dioxole;
R5 is selected from the group consisting of hydrogen and R6;
R6 represents a subgroup of the formula

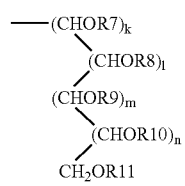

wherein
R7 is selected from the group consisting of hydrogen or $C_1$ to $C_4$ alkanoyl, or together with another substituent, selected from the group consisting of R8, R9, R10 and R11, may form a 5- or 6-ring bridged by carbonyl, or by methylene optionally substituted by $C_1$ to $C_4$ alkyl or $C_4$ to $C_5$ alkylene;
R8 is selected from the group consisting of hydrogen or $C_1$ to $C_4$ alkanoyl, or together with another substituent, selected from the group consisting of R7, R9, R10 and R11, may form a 5- or 6-ring bridged by carbonyl, or by methylene optionally substituted by $C_1$ to $C_4$ alkyl or $C_4$ to $C_5$alkylene;
R9 is selected from the group consisting of hydrogen or $C_1$ to $C_4$ alkanoyl, or together with another substituent, selected from the group consisting of R7, R8, R10 and R11, may form a 5- or 6-ring bridged by carbonyl, or by methylene optionally substituted by $C_1$ to $C_4$ alkyl or $C_4$ to $C_5$ alkylene;

R10 is selected from the group consisting of hydrogen or $C_1$ to $C_4$ alkanoyl, or together with another substituent, selected from the group consisting of R7, R8, R9 and R11, may form a 5- or 6-ring bridged by carbonyl, or by methylene optionally substituted by $C_1$ to $C_4$ alkyl or $C_4$ to $C_5$ alkylene;

R11 is selected from the group consisting of hydrogen or $C_1$ to $C_4$ alkanoyl, or together with another substituent, selected from the group consisting of R7, R8, R9 and R10, may form a 5- or 6-ring bridged by carbonyl, or by methylene optionally substituted by $C_1$ to $C_4$ alkyl or $C_4$ to $C_5$ alkylene;

k is 0 or 1;
l is 0 or 1;
m is 0 or 1, and
n is 0 or 1;

and physiologically compatible acid addition salts of compounds of formula I.

In other embodiments, the invention relates to pharmaceutical compositions comprising the compounds of formula I. In still other embodiments, the invention relates to processes for preparing compounds of formula I and intermediate products of these processes.

DETAILED DESCRIPTION

The term pharmaceutical compositions as used in the present invention means compositions comprising a pharmacologically effective quantity of a compound of the present invention and at least one pharmaceutical auxiliary and/or carrier conventional in pharmaceutical compositions.

In one embodiment, the invention provides novel 3-cyanonaphthalene-1-carboxylic acid perhydroxyalkylmethyl-piperazine compounds of formula I as described above. Where substituents in compounds of formula I stand for halogen, fluorine, chlorine or bromine are suitable. The designation (hetero)aryl is to be understood within the scope of the present invention as possibly comprising both aryl and heteroaryl radicals.

In one preferred embodiment of the present invention, R1 represents methyl.

In another preferred embodiment of the present invention, R2 and R3 each represent chlorine.

In another preferred embodiment of the present invention, R4 is selected from the group consisting of 2-furanyl, 3-furanyl, 2-thiophene, 3-thiophene, phenyl, benzyl, 2-benzofuranyl, 5-chloro-2-thiophene, 4-methylphenyl, 3,4-methylenedioxyphenyl, 2-methoxyphenyl and 4-methoxyphenyl. In a particularly preferred embodiment, R4 is selected from the group consisting of 2-furanyl, 3-furanyl, 2-thiophene, and 3-thiophene.

In another preferred embodiment of the present invention, R5 represents hydrogen.

In another preferred embodiment of the present invention, R7 and R11 each represent hydrogen; k is 1; and l, m and n are each zero.

In another preferred embodiment of the present invention, R7, R8 and R11 each represent hydrogen; k and l are each 1; and m and n are each zero.

In another preferred embodiment of the present invention, R7, R8, R9 and R11 are each hydrogen; k, l and m are each 1; and n is zero.

In another preferred embodiment of the present invention, R7 to R11 are each hydrogen; k, l and m are each 1; and n is zero.

In another preferred embodiment of the present invention, the chiral center *C is in the S configuration.

Where a substituent covered by the subgroup R6 from the group consisting of R7, R8, R9, R10 and R11 together with another substituent selected from this group stands for a 5- or 6-ring bridged by methylene optionally substituted by $C_1$ to $C_4$ alkyl or $C_4$ to $C_5$ alkylene, in particular 5- or 6-rings bridged by methylene, 1,1-dimethylmethylene, 1,1-spiro-tetramethylene-methylene or 1,1-spiro-pentamethylene-methylene are suitable. Corresponding 5- or 6-rings bridged by carbonyl are to be regarded as cyclic carbonates. In various embodiments, k stands for 1, n stands for 0, and R6 represents an optionally substituted 1,2-diol radical, a 1,2,3-triol radical or a 1,2,3,4-tetrol radical. The carbon atoms bearing the substituents R8, R9, R10 and R11 are asymmetric and may each occur in two different configurations. Due to this, R7 may occur in several stereoisomeric forms. The present invention also covers, in addition to the compounds of formula I which contain mixtures of stereoisomeric forms of the subgroup R7, compounds of formula I in which isomerically pure or substantially isomerically pure subgroups R7 are contained. Subgroups R7 include xylo-1,2,3,4-tetrahydroxybutyl, lyxo-1,2,3,4-tetrahydroxybutyl, arabino-1,2,3,4-tetrahydroxybutyl, threo-1,2,3-trihydroxypropyl, erythro-1,2,3-trihydroxypropyl and glycero-1,2-dihydroxyethyl. In one embodiment, the carbohydrates are selected from the D-series of the carbohydrates on which the subgroups R7 are based. Diastereomerically pure subgroups R7 are optionally present.

In another embodiment, the invention relates to a compound of formula I selected from the group consisting of:

3-cyano-N-[(2S)-2-(3,4-dichlorophenyl)-4-{4-[(1R,2S)-1-(2-furyl)-2,3-dihydroxypropyl]piperazin-1-yl}butyl]-N-methyl-1-naphthamide;

(2S,3R)-2-(acetyloxy)-3-{4-[(3S)-4-[3-cyano-1-naphthoyl)(methyl)amino]-3-(3,4-dichlorophenyl)butyl]piperazin-1-yl}-3-(2-furyl)propyl acetate;

3-cyano-N-[(2S)-2-(3,4-dichlorophenyl)-4-{4-[1-(2-furyl)-2-hydroxyethyl]piperazin-1-yl}butyl]-N-methyl-1-naphthamide;

3-cyano-N-[(2S)-2-(3,4-dichlorophenyl)-4-{4-[(1R,2S,3R,4R)-1-(2-furyl)-2,3,4,5-tetrahydroxypentyl]piperazin-1-yl}butyl]-N-methyl-1-naphthamide;

3-cyano-N-[(2S)-2-(3,4-dichlorophenyl)-4-{4-[(1R,2S,3S,4R)-1-(2-furyl)-2,3,4,5-tetrahydroxypentyl]piperazin-1-yl}butyl]-N-methyl-1-naphthamide;

3-cyano-N-[(2S)-2-(3,4-dichlorophenyl)-4-{4-[(1S,2S,3S,4R)-2,3,4,5-tetrahydroxy-1-(3-thienyl)pentyl]piperazin-1-yl}butyl]-N-methyl-1-naphthamide;

3-cyano-N-[(2S)-2-(3,4-dichlorophenyl)-4-{4-[(1S,2S,3R,4R)-2,3,4,5-tetrahydroxy-1-(3-thienyl)pentyl]piperazin-1-yl}butyl]-N-methyl-1-naphthamide;

3-cyano-N-[(2S)-2-(3,4-dichlorophenyl)-4-{4-[1-(2-furyl)-2-hydroxy-1-(hydroxymethyl)ethyl]piperazin-1-yl}butyl]-N-methyl-1-naphthamide;

3-cyano-N-[(2S)-2-(3,4-dichlorophenyl)-4-{4-[1-(2-furyl)-2-hydroxy-1-(hydroxymethyl)ethyl]piperazin-1-yl}butyl]-N-methyl-1-naphthamide;

3-cyano-N-[(2S)-2-(3,4-dichlorophenyl)-4-{4-[(1S,2S)-2,3-dihydroxy-1-(3-thienyl)propyl]piperazin-1-yl}butyl]-N-methyl-1-naphthamide;

3-cyano-N-[(2S)-2-(3,4-dichlorophenyl)-4-{4-[(1R,2S)-2,3-dihydroxy-1-(2-thienyl)propyl]piperazin-1-yl}butyl]-N-methyl-1-naphthamide;

3-cyano-N-[(2S)-2-(3,4-dichlorophenyl)-4-{4-[(S)-[(4S)-2-oxo-1,3-dioxolan-4-yl](3-thienyl)methyl]piperazin-1-yl}butyl]-N-methyl-1-naphthamide;

3-cyano-N-[(2S)-2-(3,4-dichlorophenyl)-4-(4-{(R)-2-furyl[(4S)-2-oxo-1,3-dioxolan-4-yl]methyl}piperazin-1-yl)butyl]-N-methyl-1-naphthamide;

3-cyano-N-[(2S)-2-(3,4-dichlorophenyl)-4-{4-[(1S,2S)-1-(3-furyl)-2,3-dihydroxypropyl]piperazin-1-yl}butyl]-N-methyl-1-naphthamide;

3-cyano-N-[(2S)-2-(3,4-dichlorophenyl)-4-{4-[1-(2-furyl)-2,3-dihydroxypropyl]piperazin-1-yl}butyl]-N-methyl-1-naphthamide;

3-cyano-N-[(2S)-2-(3,4-dichlorophenyl)-4-{4-[(1S,2S)-2,3-dihydroxy-1-phenylpropyl]piperazin-1-yl}butyl]-N-methyl-1-naphthamide;

3-cyano-N-[(2)-2-(3,4-dichlorophenyl)-4-{4-[(1S,2S)-2,3-dihydroxy-1-(4-methoxyphenyl)propyl]piperazin-1-yl}butyl]-N-methyl-1-naphthamide;

N-[(2S)-4-{4-[(1R,2S)-1-(1-benzofuran-2-yl)-2,3-dihydroxypropyl]piperazin-1-yl}-2-(3,4-dichlorophenyl)butyl]-3-cyano-N-methyl-1-naphthamide;

N-[(2S)-4-{4-[(1R,2S)-1-(5-chloro-2-thienyl)-2,3-dihydroxypropyl]piperazin-1-yl}-2-(3,4-dichlorophenyl)butyl]-3-cyano-N-methyl-1-naphthamide;

N-[(2S)-4-{4-[(1S,2S)-1-(1,3-benzodioxol-5-yl)-2,3-dihydroxypropyl]piperazin-1-yl}-2-(3,4-dichlorophenyl)butyl]-3-cyano-N-methyl-1-naphthamide; and N-[(2S)-4-{4-[(1R,2S)-1-(1-benzothien-2-yl)-2,3-dihydroxypropyl]piperazin-1-yl}-2-(3,4-dichlorophenyl)butyl]-3-cyano-N-methyl-1-naphthamide.

Process 1:

In one embodiment, compounds of the present invention may be prepared by reacting a compound of formula II

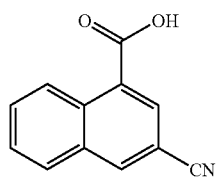

with a chlorine source, preferably oxalyl dichloride, to give a compound of formula III,

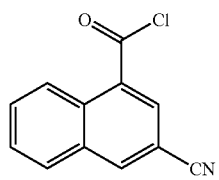

The compound of formula III is reacted with a compound of the formula IV,

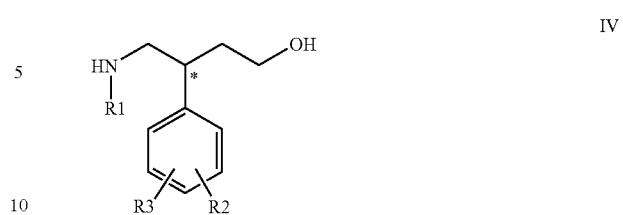

to give a compound of the formula V

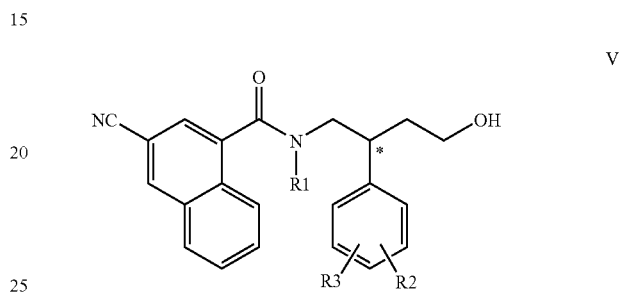

wherein R1, R2 and R3 have the meaning as defined above. The compound of formula V is reacted with methanesulfonyl chloride to give a compound of the formula VI,

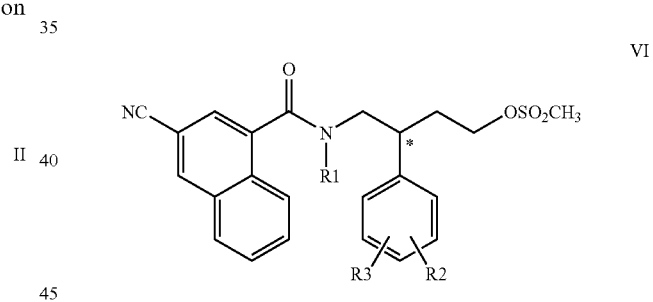

wherein R1, R2 and R3 have the meaning as defined above. The compound of formula VI is first reacted with an alkali metal halide MX wherein M stands for an alkali metal, preferably sodium and wherein X stands for halogen, preferably iodide, and subsequently reacted with a compound of formula XIX

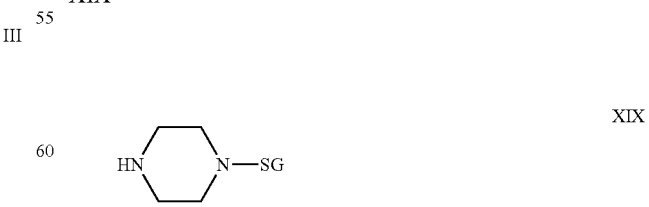

in which SG represents for a cleavable protective group, preferably tertiary butoxycarbonyl, to give a compound of the formula VIa,

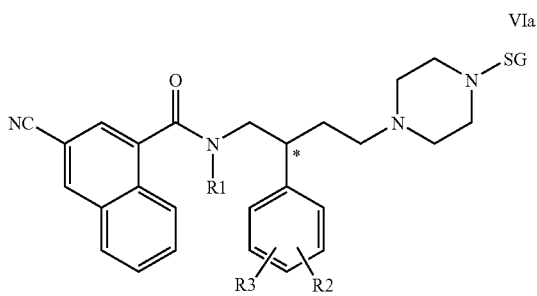

wherein R1, R2 and R3 have the meaning as defined above. The compound of formula VIa is hydrolyzed in an acidic medium to give a compound of the formula VII

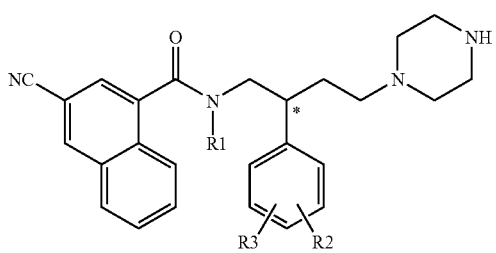

wherein R1, R2 and R3 have the meaning as defined above. The compound of formula VII is reacted with a compound of the formula VIII

R4-B(OH)$_2$     VIII and a compound of the formula IX,

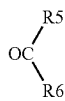

to yield a compound of formula I which is optionally converted into its physiologically compatible acid addition salt, wherein R1, R2, R3, R4, R5 and R6 have the meanings defined above.

Process 2:

In another embodiment, compounds of the present invention may be prepared by reacting a compound of the formula X

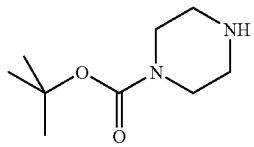

with a compound of the formula VIII

R4-B(OH)$_2$     VIII and with a compound of the formula IX,

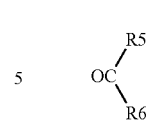

to give a compound of formula XI

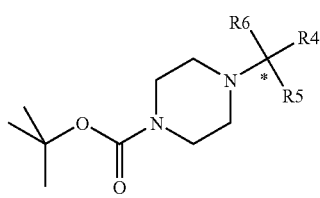

wherein R4, R5 and R6 have the meanings defined above. The compound of formula XI is then hydrolyzed in an acidic medium to give a compound of formula XII,

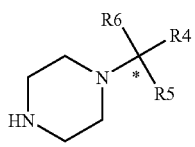

wherein R4, R5 and R6 have the meanings defined above. The compound of formula XII is reacted with a compound of formula XIII,

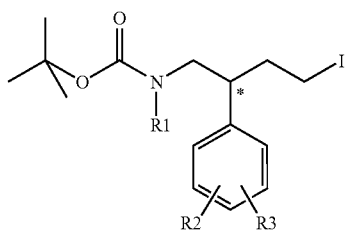

to give a compound of formula XIV,

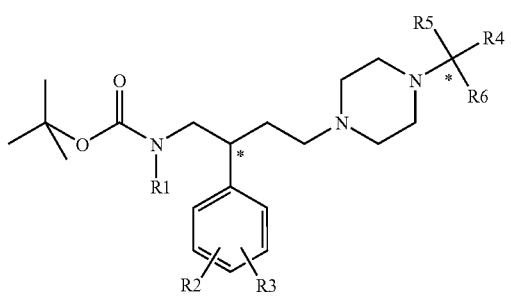

wherein R1, R2, R3, R4, R5 and R6 have the meanings defined above. The compound of formula XIV is reacted then hydrolyzed in an acidic medium to give a compound of formula XV,

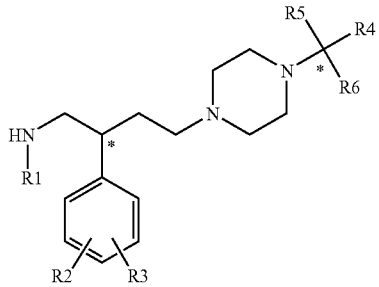

XV wherein R1, R2, R3, R4, R5 and R6 have the meanings defined above. The compound of formula XV is then reacted with a compound of formula III to yield a compound of formula I which is optionally converted into its physiologically compatible acid addition salt wherein R1, R2, R3, R4, R5 and R6 have the meanings defined above.

Process 2 may be modified in such a way that the compound of formula XII,

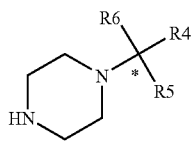

XII is reacted with a compound of formula XVI

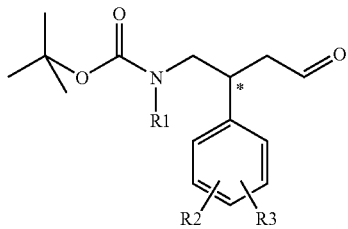

XVI to give a compound of the formula XIV wherein R1, R2, R3, R4, R5 and R6 have the meanings defined above. The compound of formula XVI

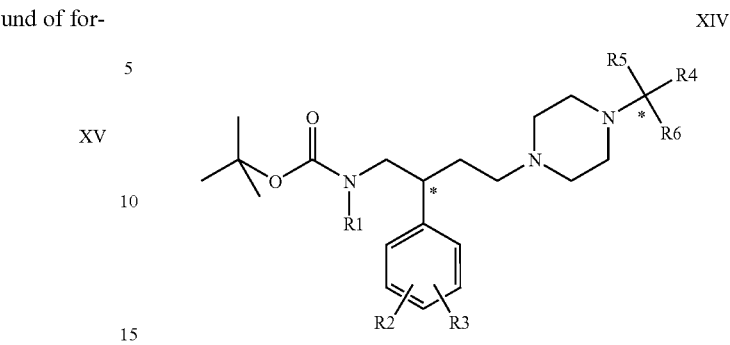

XIV is then further reacted as previously described.

Process 3:

In another embodiment, compounds of the present invention may be prepared by reacting a compound of the formula II

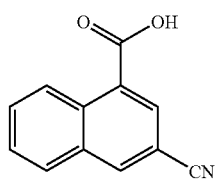

II with a chlorine source to give a compound of formula III,

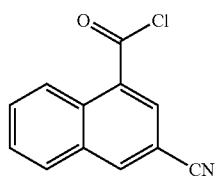

III

The compound of formula III is then reacted with a compound of the formula IV,

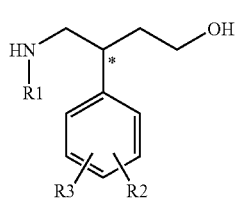

IV to give a compound of the formula V,

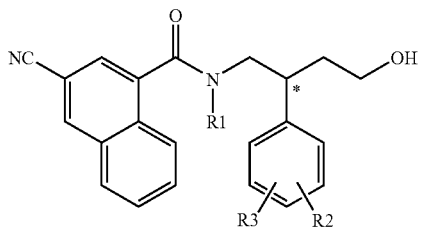

The compound of formula V is oxidized to give a compound of the formula VI,

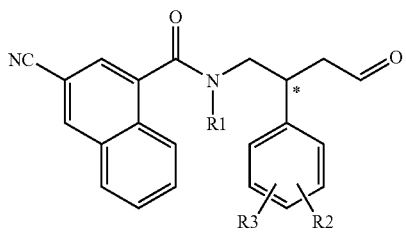

The compound of formula XVII is reacted with a compound of formula XII

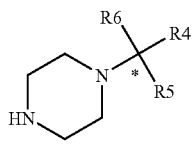

to yield a compound of formula I, which is optionally converted into its physiologically compatible acid addition salt.

The reaction of processes I and III, respectively, in which a compound of formula VII or X, respectively, is reacted with compounds of formulas VIII and IX to result in the formation of a compound of general I, can be carried out in known manner under the conditions of a boronic Mannich reaction (cf. e.g. N. A. Petasis et al., Journal of the American Chemical Society 120 (1998) 11798-11799, U.S. Pat. No. 6,232,467 (=WO 98/00398) or U.S. Pat. No. 6,602,817 (=WO 00/24510). According to this, a compound of formula VII or X can be reacted in the manner of a one-pot reaction with a boronic acid of formula VIII and a carbohydrate of formula IX which is optionally protected by suitable protective groups in a solvent which is inert under the reaction conditions. Suitable protective groups for carbohydrates are known per se, for example, from J. A. W. McOmie, "Protective Groups in Organic Chemistry", Plenum Press, 1973, or from T. W. Green, P. G. Wuts, "Protective Groups in Organic Synthesis", Wiley and Sons, 1999. Suitable solvents include dipolar-protic organic solvents such as lower alkanols, for example straight-chain or branched $C_{1-4}$-alkanols, preferably ethanol, or mixtures of these aforementioned solvents with water or with dipolar-aprotic solvents such as lower haloalkanes, preferably dichloromethane, are suitable. Suitable reaction temperatures are between room temperature and the boiling point of the solvent or of the solvent mixture. The compounds of formulas VII, X, VIII and IX may be combined in succession in this given sequence. Likewise, it is also possible, first to combine a compound of formula VII with a compound of formula IX and then with a compound of formula VII or X. The chiral center bearing the subgroups R4, R5 and R6 newly produced by this coupling reaction in compounds of formula I is usually formed with a very high degree of diastereo-control as an "anti" product.

The compounds of formula I which bear at least one free hydroxyl group in the subgroup R6 may if desired then also be reacted with carboxylic acids $R^{12}COOH$ of formula XVII, wherein R12 has the meaning of straight-chain or branched alkyl with 1 to 3 carbon atoms, whereby the free hydroxyl groups of the subgroup R6 are acylated. Usually under these circumstances peracylation of the free hydroxyl groups of the subgroup R6 takes place. The acids of formula XVII or their reactive derivatives may be used as acylation agents. In particular acid anhydrides and acid halides are suitable reactive derivatives. The acylation may be carried out in an organic solvent which is inert under the reaction conditions, preferably at temperatures between −20° C. and room temperature. Suitable solvents are in particular aromatic hydrocarbons such as benzene or toluene, cyclic or open-chain di-lower alkyl ethers such as diethyl ether, tetrahydrofuran (=THF) or dioxane, partially halogenated lower hydrocarbons such as dichloromethane or mixtures of these solvents. Where an acid anhydride or an acid halide of the acids of formula XVII is used as acylation agent, the acylation may expediently take place in the presence of an acid-binding reagent. Suitable acid-binding reagents are non-nucleophilic organic bases soluble in the reaction mixture, such as pyridine, triethylamine or 4-dimethylaminopyridine. Organic bases used in excess can simultaneously also be used as solvents.

The compounds of formula I which bear at least two free hydroxyl groups in the subgroup R6 may if desired, after their preparation described above, also be reacted with a reactive carbonyl-synthesis equivalent, instead of a reaction with compounds of formula XVII, whereby the subgroup R6 can be carbonylated. The reaction can take place in known manner. For example, a compound of formula I can be reacted in an organic solvent which is inert under the reaction conditions. Suitable reactive carbonyl synthesis equivalents are for example phosgene or substances which react like phosgene, such as bis-(trichloromethyl)carbonate (=triphosgene), trichloromethyl chloroformate (=diphosgene) or in particular carbonyldiimidazole. Expediently an acid-binding reagent may be added to the reaction mixture. Suitable acid-binding reagents are the acid-binding reagents given above for the reaction of compounds of formula I with compounds of formula XVII. Suitable reaction temperatures are between about −20° C. and room temperature.

The compounds of formula I which bear at least two free hydroxyl groups in the subgroup R6 may if desired, after their preparation described above, instead of a reaction with compounds of formula XVII or instead of a reaction with reactive carbonyl synthesis equivalents, also be reacted with a di-lower alkyl ketone or a $C_{5-6}$-cycloalkyl ketone in the subgroup R6, to produce a 5- or 6-ring derivative bridged [by] methylene optionally substituted by lower alkyl or $C_{4-5}$-alkylene. Acetone is suitable as di-lower alkyl ketone. Cyclopentanone and cyclohexanone are suitable as $C_{5-6}$-cycloalkyl ketones.

Where compounds of formula I are to be prepared in which the substituents contained in the subgroup R6, R7, R8, R9, R10 and/or R11 have meanings other than hydrogen, the point of departure is preferably carbohydrate compounds of Formula IX which contain free hydroxyl groups at least in alpha-position to the aldehyde function. It is beneficial to start with compounds of formula IX wherein R7, R8, R9, R10 and R11 are hydrogen. The free hydroxyl groups may if desired then be acylated, carbonylated or reacted with a suitable ketone in the above manner.

The compounds of formula VII are novel compounds which are advantageously suitable as intermediate products for the preparation of novel active substances, for example for the preparation of the compounds of formula I, which are antagonistic to tachykinin receptors.

The compounds of formula VII can be prepared by reacting a compound of the formula VI,

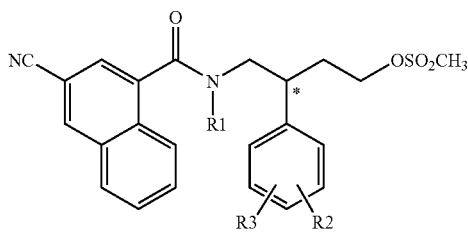

VI wherein R2 and R3 have the above meanings, with an alkali metal halide MX wherein M stands for an alkali metal, preferably sodium, and wherein X represents halogen, preferably iodide, and a protected piperazine derivative of the formula XIX,

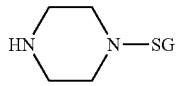

XIX wherein SG represents a cleavable protective group, in particular tert. butoxycarbonyl, to give compounds of the formula VIa and subsequently cleaving off the protective group SG again in known manner to give compounds of formula VII. The reaction can be carried out in an organic solvent which is inert under the reaction conditions, such as an aromatic hydrocarbon, in particular toluene, or in a cyclic or open-chain di-lower alkyl ether, in particular THF, or preferably in a mixture of the aforementioned solvents and in the presence of a base. Suitable bases are non-nucleophilic organic nitrogen bases such as tertiary lower alkylamines, for example triethylamine. Suitable reaction temperatures are between 50° and 100° C., preferably approximately 70° to 90° C.

Compounds of formula VI can be prepared by reacting compounds of the formula V,

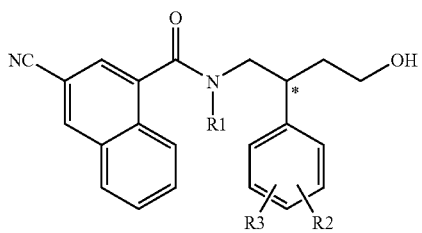

V wherein R1, R2 and R3 have the above meanings, in known manner with methanesulfonyl chloride. Compounds of formula VI and their stereoisomeric forms are known per se, for example from U.S. Pat. No. 5,236,921 (=EP 474,561), and can be prepared according to the processes described in this specification or according to analogous processes.

Compounds of formula XIII can be prepared by reacting compounds of the formula IV,

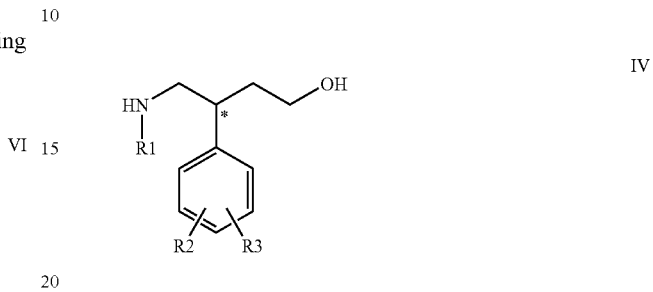

IV with tertiary butyloxycarbonyl anhydride to give a compound of formula XX,

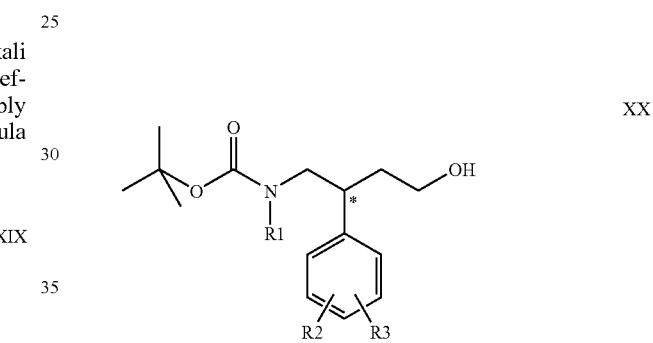

XX wherein R1, R2 and R3 have the above meanings. The compounds of the formula XX are further reacted with methanesulfonyl chloride to give compounds of formula XXI

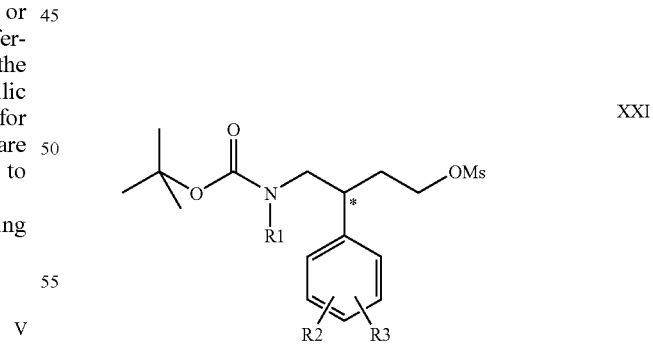

XXI wherein R1, R2 and R3 have the above meanings. The compounds of formula XXI are subsequently reacted with an alkali metal halide MX wherein M represents an alkali metal, preferably sodium and wherein X represents halogen, preferably iodide to give compounds of formula XIII

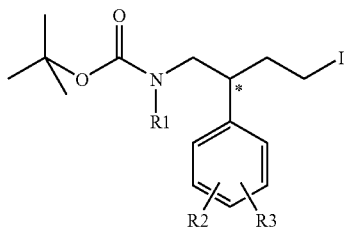

XIII wherein R1, R2 and R3 have the above meanings.

The compound of formula XVI can be prepared by oxidation of compound XX in any manner known from the art, e.g, by dimethylsulfoxide activated with oxalyl chloride (Swern oxidation).

The compounds of formulas VIII, IX and XIX are known per se or can be prepared by a skilled chemist from known compounds in a known manner. Compounds of formula IX which are preferentially used, include D-xylose, D-lyxose, D-arabinose, D-threose, D-erythrose and D- and L-glyceraldehyde.

The compounds of formula I may be isolated from the reaction mixture and purified in known manner. Acid addition salts may be converted into the free bases in conventional manner, and these may if desired be converted in known manner into physiologically compatible acid addition salts. Physiologically compatible salts of compounds of formula I are their conventional salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or trifluoromethanesulfonic acid, or benzenesulfonic acids optionally substituted in the benzene ring by halogen or lower alkyl, such as p-toluenesulfonic acid.

The compounds of formula I contain in the alpha-position to the ring nitrogen atom in the 4-position of the piperazine ring an asymmetrical carbon atom, namely the carbon atom *C bearing the phenyl ring substituted by R2 and R3. Due to this asymmetrical carbon atom and to the asymmetrical carbon atom bearing the subgroups R4, R5 and R6 and optionally also due to the asymmetrical carbon atoms contained in the subgroup R6, the compounds of formula I may be present in several stereoisomeric forms. The present invention covers both the mixtures of optical isomers and the isomerically pure compounds of formula I. Preferred are compounds of formula I in which the carbon atom *C bearing the phenyl ring substituted by R2 and R3 is in the S-configuration.

If mixtures of optical isomers of the starting compound, for example of the compounds of formula VII or the compounds of formula IX, are used in the synthesis of the compounds of formula I, the compounds of formula I are also obtained in the form of mixtures of optical isomers. Starting from stereochemically uniform forms of the starting compound, stereochemically uniform compounds of formula I can also be obtained. The stereochemically uniform compounds of formula I can be obtained from the mixtures of optical isomers in known manner, for example by chromatographic separation on chiral separating materials or by reaction with suitable optically active acids, for example tartaric acid or 10-camphorsulfonic acid, and subsequent separation into their optically active antipodes by fractional crystallization of the diastereomeric salts obtained.

The compounds of formula I and their acid addition salts have properties which are antagonistic to tachykinin receptors and are therefore suitable for the treatment of pathological conditions in larger mammals, particularly humans, in which tachykinins are involved as transfer agents. The group of compounds according to the invention is distinguished by a particularly beneficial activity profile which is characterized by a high selective affinity to $NK_1$- and $NK_2$ receptors. Furthermore, the group of compounds according to the invention is distinguished by good compatibility even over prolonged periods of administration, and by comparatively good oral availability. Due to their activity profile, the compounds of formula I are particularly suitable for inhibiting processes in which tachykinins, such as neurokinin A, which bind to $NK_1$ and to $NK_2$ receptors are involved.

Owing to the action which is advantageously directed at the peripheral region, the compounds of formula I are suitable in particular for the treatment and/or inhibition of respiratory diseases, in particular asthma, bronchitis, cough, and rhinitis; skin diseases, in particular inflammatory skin reactions, allergic skin reactions, and psoriasis; arthropathic diseases, in particular arthritis, vasculitides and systemic lupus erythematosus; functional or inflammatory disorders in the gastrointestinal tract, in particular pseudomembranous colitis and diarrhea; bleb diseases such as cystitis and interstitial cystitis; and migraine, of larger mammals, particularly humans, of both sexes, also including diseases which involve increased sensitivity to pain and/or impaired stool passage in the colon region.

The functional disorders in the gastrointestinal tract which can be treated by the compounds according to the invention include in particular the disorders of the lower intestinal tracts known under the name "irritable bowel syndrome" (=IBS). Typical symptoms for the diagnosis of IBS are described, for example, in W. G. Thompson et al., Gastroenterology International 2 (1989) 92-95 or in W. G. Thompson et al., GUT 45/II (1999) II43-II47, and are generally known among experts by the term "Rome Criteria". The essential symptoms of IBS accordingly include pains in the lower abdomen, which appear to be due to hypersensitivity of the visceral afferent nervous system, and anomalies in bowel movement, such as constipation, diarrhea or alternating constipation and diarrhea.

Further inflammatory disorders in the gastrointestinal tract which can be beneficially influenced by the group of compounds according to the invention are for example the inflammatory disorders in the small intestine and large intestine regions usually covered by the term "inflammatory bowel disease" (=IBD), for example ulcerative colitis or Crohn's disease.

Owing to their mechanism of action, the compounds of the invention furthermore appear suitable for the treatment of other disorders in which tachykinins and in particular neurokinin A are involved as transfer agents. These disorders include for example neurogenic inflammations, inflammatory joint diseases such as rheumatic arthritis, asthmatic complaints, allergic disorders, disorders of immune regulation, bladder inflammation or also functional dyspepsia.

Description of Pharmacological Test Methods

The example numbers given for the compounds of formula I used as test substances in the pharmacological tests given below relate to the preparation examples described below.

1. Determination of the Binding Power of the Test Substances to $NK_1$ Receptors In Vitro.

Affinity of the test substances to human $NK_1$ receptors was measured in vitro. The inhibition of the binding of the physiological neurokinin (Substance P) to neurokinin-1 receptors was determined.

The receptor binding studies were performed with [$^3$H]-Substance P as ligand. For the binding test, different samples of a membrane preparation of CHO cells (=egg cells of the Chinese hamster, Chinese hamster oocytes), which express the human $NK_1$ receptor ("Accession Number" of the associated nucleic acid sequence=M74290; "Accession Number" of the associated protein sequence=P25103; cf. Takeda, Y.; Chou, K. B., Takeda, J.; Sachais, B. S. and Krause, J. E; Biochemical and Biophysical Research Communications, 179(3) (1991) 1232-1240), were incubated with a solution of the marked ligand, with the incubation mixtures containing no test substance or additions of different concentration of test substance. Then, separation of bound and free ligands was performed in each of the samples with the aid of glass-fiber filtration. The fraction remaining in the filter was washed several times with buffer solution and then the radioactivity of the fraction remaining in the filter was measured using a beta scintillation counter.

For the compounds of Examples 1 to 14, that concentration which effects half maximum displacement of the bound ligand was determined as $IC_{50}$ of the respective test substance. From this, the corresponding inhibition constant ($K_i$ value) of the test substance was calculated, and was stated as the negative common logarithm of the $K_i$ value (=$pK_i$ value) The $pK_i$ value is a measurement of the affinity of the test substances to human $NK_1$ receptors. In this test model, the test substances set forth in the following Table 1 exhibited the given $pK_i$ values:

TABLE 1

Affinity of the test substances to human $NK_1$ receptors

| Compound No. | pKi (NK$_1$) |
|---|---|
| 1 | 8.4 |
| 2 | 8.5 |
| 3 | 8.8 |
| 4 | 8.6 |
| 5 | 8.9 |
| 6 | 8.3 |
| 7 | 8.3 |
| 8 | 8.1 |
| 9 | 8.0 |
| 10 | 8.0 |
| 11 | 8.1 |
| 12 | 8.0 |
| 13 | 8.1 |
| 14 | 8.3 |
| 16 | 9.0 |
| 17 | 7.5 |
| 18 | 8.5 |
| 21 | 8.7 |
| 22 | 8.4 |
| 24 | 8.0 |
| 25 | 8.1 |
| 26 | 8.1 |
| 27 | 8.2 |
| 28 | 7.9 |

All the aforementioned test substances exhibited pKi values of at least 7.0 in this test model. The compounds of Examples 1 to 14 exhibited pKi values of at least 7.9.

2. Determination of the Binding Power of the Test Substances to $NK_2$ Receptors In Vitro The affinity of the test substances to human $NK_2$ receptors was measured in vitro. The ability of the test substances to displace the selective $NK_2$ receptor antagonist SR 48968 (=saredutant) used as reference ligand from its corresponding bond was determined.

The receptor binding studies were carried out with radioactively marked [$^3$H]-SR 48968 (from Amersham) as ligand. For the binding test, different samples of a membrane preparation of CHO cells (=egg cells of the Chinese hamster, Chinese hamster oocytes), which express the human $NK_2$ receptor (for preparation, see N. P. Gerard et al., Journal of Biological Chemistry 265/33 (1990) 20455-20462), were incubated for 90 minutes (=min.) with a solution of the marked ligand, with the incubation mixtures containing no test substance or additions of different concentrations of test substance. Then in each case the membrane-bound ligands in the samples were separated from free ligands by filtration. The fraction remaining in the filter was washed several times with buffer solution, before its radioactivity was measured using a liquid scintillation counter. That concentration which effects half-maximum displacement of the bound reference ligand was determined as $IC_{50}$ of the respective test substance. The inhibition constant (Ki value) of the test substance was calculated from the respective $IC_{50}$ value, and was stated as the negative logarithmized value thereof (pKi).

For the compounds of Examples 1 to 14, the affinity to human $NK_2$ receptors was determined in each case by at least three measurements of the test substances in concentration series of $10^{-6}$ to $10^{-10}$ mol/l. If several measurements were performed, the average thereof was listed each time. The $pK_i$ value is a measurement of the affinity of the test substances to human $NK_2$ receptors. In this test model, the test substances set forth in the following Table 2 exhibited the given $pK_i$ values:

TABLE 2

Affinity of the test substances to human $NK_2$ receptors

| Compound No. | pKi (NK$_2$) |
|---|---|
| 1 | 8.1 |
| 2 | 7.1 |
| 3 | 7.2 |
| 4 | 6.9 |
| 5 | 7.3 |
| 6 | 7.4 |
| 7 | 7.4 |
| 8 | 7.5 |
| 9 | 7.2 |
| 10 | 7.0 |
| 11 | 7.6 |
| 12 | 7.0 |
| 13 | 7.7 |
| 14 | 7.9 |
| 16 | 6.1 |
| 17 | 5.5 |
| 18 | 6.8 |
| 21 | 6.4 |
| 22 | 6.0 |
| 24 | 7.5 |
| 25 | 7.4 |
| 26 | 7.0 |
| 27 | 7.6 |
| 28 | 7.3 |

All the aforementioned test substances exhibited pKi values of at least 7.0 in this test model. The compounds of Examples 1 to 14 exhibited pKi values of at least 6.9.

3. Determining of the Functional $NK_1$ Antagonism of the Test Substances on Isolated Guinea Pig Tissue In Vitro The action antagonistic to $NK_1$ receptors of the test substances was measured in vitro on isolated ring preparations, kept in an oxygenated nutrient solution, of the aortas of Pirbright-White guinea pigs. The inhibition by the test substances of the relaxation of tone of the aorta preparations, caused after stimulation with the $NK_1$ agonist Substance P, was determined.

In order to measure the contraction of the vessel muscles, the preparations were fixed to a hook, joined by a thread to a force measuring apparatus and the contractions were recorded in each case on a plotter. The aorta preparations were tonicized with phenylephrine. Then before and after the administration of the test substance the $NK_1$ receptors of the preparations were stimulated with 0.01 μmol Substance P, which caused relaxation of the tone. The relaxations before and after the administration of the test substance were qualified in percent. The effective concentration of the half maximum inhibition of the relaxation of the tone (=$EC_{50}$) was calculated. The negative common logarithm of the $EC_{50}$ value (=$pEC_{50}$) was given as characteristic variable. The $pEC_{50}$ value is a measurement of the functional effectiveness of the test substances on $NK_1$ receptors. In this test model, the test substances set forth in Table 3 below exhibited the given $pEC_{50}$ values:

TABLE 3

Functional $NK_1$ antagonism of the test substances on isolated guinea pig tissue

| Example No. | $pEC_{50}$ |
| --- | --- |
| 1 | 9.4 |
| 2 | 9.5 |
| 5 | 10.0 |
| 6 | 9.4 |
| 11 | 8.9 |

4. Determination of the Functional Agonism of the Test Substances on Isolated Guinea Pig Tissue In Vitro.

The $NK_2$ receptor-antagonizing action of the test substances was determined on isolated gall-bladder preparations from Pirbright-White guinea pigs, held in an oxygen-saturated nutrient solution. To this end, the preparations were fastened on one hand in the nutrient solution to organ holders and on the other hand on a force meter by a thread.

In this test the $NK_2$ receptors present in the gall-bladder preparations were stimulated with the natural $NK_2$ receptor agonist neurokinin A (=NKA; 0.1 μmol/l) and the contractions of the preparations caused thereby were measured as contractility in mN (=preliminary value) measured. Then NKA was rinsed out of the preparations with NKA-free solution and the test substances were added in a concentration of $10^{-7}$ mol/l. After two hours' incubation of the preparations with the test substances, the contractions of the preparations then still caused by renewed NKA addition were again measured and the results were given as percentages, relative to the contractions initially measured, caused solely by NKA addition. The concentration of the test substances was increased iteratively in the subsequent experiments as a function of the result in logarithmic whole or half steps, until at least one concentration above or below 50% inhibition of contraction was determined (up to at most $10^{-5}$ mol/l). For each concentration, the average value of inhibition of contraction was calculated from 2 to 4 preparations. In each case, the concentration of half-maximum inhibition ($IC_{50}$) per test substance was calculated as characteristic variable. In each case the logarithmized value of the $IC_{50}$ per test substance is given as $pIC_{50}$ in [mol/l]. In this test model, the test substances set forth in Table 4 below exhibited the $pIC_{50}$ value given below.

TABLE 4

Functional $NK_2$ antagonism of the test substances on isolated guinea pig tissue

| Example No. | $pIC_{50}$ |
| --- | --- |
| 1 | 8.7 |
| 2 | 7.7 |
| 5 | 7.5 |
| 6 | 7.4 |
| 11 | 7.8 |

5. Functional Cellular Tests of the $NK_1$- and $NK_2$-antagonistic Effects

Functional cellular tests of the antagonistic effect of the compounds of the present invention on the human tachykinin receptors were performed in CHO cells expressing the recombinant human $NK_1$ or $NK_2$ receptor. In these tests the inhibition of ligand induced increase in mobilization of intracellular calcium and the inhibition of ligand induced phosphorylation of MAPK were determined, which can be used as a measure of functional activity of tachykinin-antagonists. Additionally, the antagonistic properties of reference compounds on the different tachykinin receptors were characterized for comparison.

The effects of test compounds were assessed using Chinese hamster ovary (CHO) fibroblast cells, stably expressing cloned human $NK_1$ or $NK_2$ receptors. The NK receptor in coupled to $G_q$. The activation of the $G_q$ protein by ligand binding to the receptor leads to a mobilization of intracellular calcium and phosphorylation of MAPK. Both systems were used to determine functional effects of the test compounds.

$Ca^{2+}$ Measurements Using FLIPR for $NK_1$ and $NK_2$ Activity

For tests, cell were seeded 24 hours prior to the experiment into black 96-well microplates. The cell density was $2.2 \times 10^4$ cells/well. All steps were done under sterile conditions. In order to observe changes in intracellular calcium levels, cells were loaded with a calcium-sensitive dye. This dye (FLUO-4, from Molecular Probes) excites at 488 nm, and emits in the 560 nm range, only if a complex with calcium is formed. For the dye loading the growth-medium was aspirated out of the well without disturbing the confluent cell layer and 100 μl loading medium (HBSS, 4 μM FLUO-4, 0.005% (w/v) pluronic acid, 2.5 mM probenecid, 20 mM HEPES, pH 7.4) was dispensed into each well using an automatic pipettor system (Multidrop, Labsystems). Pluronic acid was added to increase dye solubility and dye uptake into the cells, whereas probenecid, an anion exchange inhibitor, was added to the loading medium to increase dye retention in the cells. The cells were incubated in a 5% $CO_2$ incubator at 37° C. for 40 minutes. After dye loading, the cells were washed three times with wash-buffer (HBSS, 2.5 mM probenecid, 20 mM HEPES, pH 7.4) to reduce basal fluorescence. In the last washing step the buffer was aspirated and replaced with 100 μl washing buffer. For the antagonism screening mode 50 μl of the compound (final concentration ranges from 10 μM to 1.4 nM) were applied 7 min prior to addition of substance P (final concentration: $10^{-8}$M; $NK_1$ agonist) or NKA (final concentration: $10^{-7}$ M; $NK_2$ agonist). The FLIPR setup parameters were set to 0.4 sec exposure length, filter 1, 50 μl fluid addition, pipettor height at 125 μl, dispense speed 40

μl/sec without mixing. Maximal fluorescence changes were obtained using the statistic function of the FLIPR software, and data plotted using GraphPad Prism 4. All points were expressed as a percentage inhibition of the control agonist. $IC_{50}$ values were determined using sigmoidal dose-response curve fitting. Antagonist potencies ($pA_2$) values were calculated using equation:

$$pA_2 = -\log(IC_{50}/(1+[L]/EC_{50})),$$

in which the $IC_{50}$ of the test compound was obtained from concentration-effect relationships, [L] is the concentration of the agonist (substance P for $NK_1$ test, NKA for $NK_2$ test), and the $EC_{50}$ is the potency of the agonist at the respective human cloned NK receptor ($EC_{50}$ substance P: $10^{-9.6}$M; $EC_{50}$ NKA: $10^{-8.8}$M). The results are summarized in Table 5:

TABLE 5

$pA_2$ data for $NK_1$ and $NK_2$:

| Compound No. | $pA_2$ ($NK_1$) | $pA_2$ ($NK_2$) |
|---|---|---|
| 1 | 8.9 | 8.0 |
| 7 | 8.8 | 8.1 |
| 8 | 9.2 | 8.9 |
| 9 | 8.5 | 8. |
| 13 | 8.3 | 7.7 |
| 14 | 9.4 | 8.5 |
| 16 | 9.3 | 9.1 |
| 17 | 7.7 | 7.7 |
| 18 | 8.2 | 8.6 |
| 21 | 9.1 | 9.5 |
| 22 | 8.1 | 8.5 |
| 24 | 8.1 | 7.8 |
| 25 | 8.5 | 9.0 |
| 26 | 8.0 | 7.4 |
| 27 | 9.2 | 8.1 |
| 28 | 8.7 | 7.6 |

6. Determination of the $NK_1$- and $NK_2$-receptor-antagonistic Effectiveness of the Test Substances In Vivo The $NK_1$- and $NK_2$-antagonistic activities of the test substances were investigated in anesthetized guinea pigs in each case after intravenous (=i.v.) and oral (=p.o.) administration in vivo. With the present test model it is possible to detect both $NK_2$-antagonistic effects in three different organ systems (respiratory tracts, colon and circulation) and $NK_1$-antagonistic effects (rapid drop in blood pressure) in an animal simultaneously.

Pirbright-White guinea pigs having a body weight of 500-700 g were anesthetized with ketamine/xylazine (67/13 mg/kg subcutaneously, initial dose, further doses administered as required). The animals were provided with an intravenous catheter in order to administer the substance and an intra-arterial catheter to measure the blood pressure. The animals were artificially ventilated via a tracheal cannula and the respiratory pressure was recorded by a pressure transducer. A balloon was introduced into the distal colon of the animals for manometric recording of colon motility by a pressure transducer. Blood pressure, heart rate, respiratory pressure and colonic pressure were measured continuously for each animal and plotted on a recorder and by a digital data-processing system. Neurokinin A (=NKA; 200 pmol/animal) was administered i.v. as a bolus as a test stimulus to stimulate the $NK_1$- and the $NK_2$-receptors. An addition of NKA of this type results in a great increase in respiratory pressure (bronchoconstriction) and colonic pressure, and in a biphasic drop in blood pressure. The first phase of hypotension (=phase of maximum hypotension within the first minute after administration of NKA) is mediated via $NK_1$ receptors, since they can be blocked completely by specific $NK_1$ receptor antagonists. The second phase of delayed hypotension (=phase of maximum hypotension after 2-5 min.) on the other hand is mediated via $NK_2$ receptors, since they can be blocked by specific $NK_2$ receptor antagonists. The doses of the test substances are given as $ED_{50}$ values which each result in a response to the NKA test stimulus which is reduced to 50% of the initial value, as characteristic variables for the individual measurement parameters bronchoconstriction, colonic pressure and change in blood pressure mediated by $NK_1$ or $NK_2$.

TABLE 6

$NK_1$- and $NK_2$-receptor-antagonistic effectiveness of the test substances of Formula I on guinea pigs in vivo after intravenous administration $ED_{50}$ iv [μmol/kg] after 1 min (cumulative)

| Structure | $NK_1$ (early hypotension) | $NK_2$ (late hypotension) | $NK_2$ (bronchoconstriction) | $NK_2$ (colonic motility) |
|---|---|---|---|---|
| 1 | 0.077 | 0.643 | 0.321 | 0.027 |
| 2 | <0.010 | 0.106 | <0.010 | 0.085 |
| 6 | 0.071 | 0.282 | 0.595 | 0.050 |
| 7 | 0.052 | 0.338 | 0.207 | 0.309 |
| 8 | 0.070 | 0.803 | 1.126 | 0.135 |
| 9 | 0.099 | 1.044 | 0.943 | 0.287 |
| 10 | 0.041 | 0.040 | 0.045 | 0.109 |
| 11 | 0.093 | 0.145 | 0.130 | 0.132 |
| 23 | 0.029 | 1.165 | 0.725 | 0.961 |

The antagonistic effects of the test substances were first investigated in cumulative form, the time of the NKA test stimulus being 1 min after the administration of the respective doses of the test substances had ended. These $ED_{50}$ values obtained from cumulative dose effect curves are plotted in Table 6.

The measured values plotted in Table 6 above show, inter alia, that the substances of structures 1, 2 and 6 to 11 after cumulative administration i.v. (detection of the antagonism 1 min. after the administration of test substance had ended) caused a marked $NK_1$-receptor-antagonistic activity on the early hypotension as well as $NK_2$-receptor-antagonistic activity on colon motility, late drop in blood pressure and respiratory resistance.

In order additionally to detect the variation over time of the antagonistic effects of the test substances, the action of the NKA test stimulus was determined at different times (1, 30, 90, 120, 150 and 180 min.) after oral administration of the test substances. The antagonistic effects of the test substances were then determined as "area under the curve" ("AUC") over the investigation period after administration of the test substances (1-180 min after administration) and the $ED_{50}$ values after oral administration obtained therefrom were plotted in Table 7.

TABLE 7

$NK_1$- and $NK_2$-receptor-antagonistic effectiveness of the test substances of Formula I on guinea pigs in vivo after oral administration $ED_{50}$ $AUC_{1-180\,min}$ oral [μmol/kg]

| Structure | $NK_1$ (early hypotension) | $NK_2$ (late hypotension) | $NK_2$ (bronchoconstriction) | $NK_2$ (colonic motility) |
|---|---|---|---|---|
| 1 | 22.9 | 3.1 | 3.1 | 5.5 |
| 2 | 15.2 | 14.8 | 11.7 | 6.0 |

These tests show that the compounds according to the invention, in particular the substance of structures 1 and 2 as shown in Table 7, are furthermore active orally as $NK_2$ as well as $NK_1$ receptor antagonists.

The compounds of formula I may be administered in conventional pharmaceutical preparations. The doses to be used may vary individually and will naturally vary according to the type of condition to be treated and the substance used. In general, however, medicinal forms with an active substance content of about 0.2 to about 200 mg, or about 1 mg to about 50 mg, active substance per individual dose are suitable for administration to humans and larger mammals and may be administered one to a small plurality (i.e. about 6) of times per day. The compounds may be contained according to the invention, together with conventional pharmaceutical auxiliaries and/or carriers, in solid or liquid pharmaceutical preparations. Examples of solid preparations include preparations which can be administered orally, such as tablets, coated tablets, capsules, powders or granules, or alternatively suppositories. These preparations may contain conventional pharmaceutical inorganic and/or organic carriers, such as talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or carriers in known manner. For the production of solid pharmaceutical dosage forms, the active substances may for example be mixed with the auxiliaries and/or carriers in conventional manner and may be wet or dry granulated. The granules or powder can be filled directly into capsules or be pressed into tablet cores in conventional manner. These may be coated in known manner, if desired.

The following examples are intended to illustrate the invention in further detail, without restricting its scope.

EXAMPLE 1

3-cyano-N-[(2S)-2-(3,4-dichlorophenyl)-4-{4-[(1R, 2S)-1-(2-furyl)-2,3-dihydroxy-propyl]-piperazin-1-yl}butyl]-N-methyl-1-naphthamide (process 1)

A) 58.0 g 3-cyano-naphthalene-1-carboxylic acid (formula II) was suspended in 600 ml of dichloromethane. 2 ml of DMF were added successively under stirring. To this initial suspension, 35 ml of oxalyl dichloride in 65 ml dichloromethane were added slowly. The mixture was stirred for 4 hours at 30° C. to 40° C. The obtained solution was concentrated to dryness and 67 g of 3-cyano-naphthalene-1-carbonyl chloride (formula III) was isolated, stored in a refrigerator and used without further purification.

B) 20 g of 3S-(3,4-Dichloro-phenyl)-4-methylamino-butan-1-ol (formula IV) were suspended in 200 ml of THF under stirring at room temperature. 12 g of KOH dissolved in 100 ml of water were added leading to a solution. 17.2 g of 3-cyano-naphthalene-1-carbonyl chloride (formula II, from reaction step A)) were added and stirred for 3 hours. The organic solvents were eliminated and the remaining mixture was supplemented with ethyl acetate and methyl-tert.-butyl ether. The water phase was eliminated while the organic phase was washed four times with 50 ml of water and dried over sodium sulfate. The organic phase was concentrated to dryness, providing 31.8 g of a yellowish solid (3-cyano-naphthalene-1-carboxylic acid [2S-(3,4-dichloro-phenyl)-4-hydroxy-butyl]-methyl-amide; formula V) which was used without further purification.

C) 5.8 g of 3-cyano-naphthalene-1-carboxylic acid [2S-(3,4-dichloro-phenyl)-4-hydroxy-butyl]-methyl-amide (formula V, from reaction step B)) were dissolved in 100 ml dichloromethane. 2.2 ml of triethylamine and 1.16 ml of methanesulfonyl chloride were added at room temperature. The reaction mixture was stirred for 5 hours and left for 2.5 days. Water was added and the organic part was dried over sodium sulfate and concentrated to dryness. 6.65 g of a foamy product (3-cyano-naphthalene-1-carboxylic acid [(2S)-2-(3,4-dichloro-phenyl)-4-methylsulfonyl-butyl]-methyl-amide, formula VI) were isolated and used without further purification.

D) 6.65 g of 3-Cyano-naphthalene-1-carboxylic acid [2S-(3, 4-dichloro-phenyl)-4-methylsulfonyl-butyl]-methyl-amide (formula VI, from reaction step C)) were dissolved in 150 ml of acetonitrile. 1.84 g of potassium iodide, 2.44 g N-tert. butoxycarbonyl-piperazine (formula XIX) and 2.2 ml triethylamine were added and the mixtures was heated to reflux for three hours. After cooling down to room temperature, the reaction mixture was left over night before adding water and ethyl acetate. The organic phase was washed with water and a saturated solution of sodium bicarbonate. Drying of the organic phase over sodium sulfate and evaporation of the solvent in a vacuum yielded 7.8 g 3-cyano-naphthalene-1-carboxylic acid {2S-(3,4-dichloro-phenyl)-4-[4-(2,2-dimethyl-propionyl)-piperazin-1-yl]-butyl}-methyl-amide (formula VIa), which was used directly for further reactions without further purification.

E) 6.6 g 3-cyano-naphthalene-1-carboxylic acid {2S-(3,4-dichloro-phenyl)-4-[4-(2,2-dimethyl-propionyl)-piperazin-1-yl]-butyl}-methyl-amide (formula VIa, from reaction step D)) were dissolved in 150 ml ethanol and 20 ml of 5N HCl were added. The mixtures was stirred for 2 days and neutralized with sodium carbonate. Ethanol was distilled off and the product was extracted with ethyl acetate and water. The ethyl acetate layer was dried over sodium sulfate and concentrate to dryness, providing 5.2 g of amorphous 3-cyano-naphthalene-1-carboxylic acid [2S-(3,4-dichloro-phenyl)-4-piperazin-1-yl-butyl]-amide (formula VIII).

F) 3.0 g of 3-cyano-naphthalene-1-carboxylic acid [2S-(3,4-dichloro-phenyl)-4-piperazin-1-yl-butyl]-amide (formula VII, from reaction step E)), 806 mg of 2-furanboronic acid (formula VIII) and 945 mg of 80% pure (D)-glyceraldehyde (formula IX) in ethanol were heated to reflux for 5 hours. The mixture was kept at room temperature over night before distilling off the organic solvent. The product obtained was purified by column chromatography (ethyl acetate till ethanol) to deliver 1.3 g of pure crystalline 3-cyano-N-[(2S)-2-(3,4-dichlorophenyl)-4-{4-[(1R,2S)-1-(2-furyl)-2,3-dihydroxypropyl]piperazin-1-yl}butyl]-N-methyl-1-naphthamide (formula I).
$[\alpha]_D^{20}=-27.6°$ (c=1, methanol).
MS-data (ES+): M+ bei m/z=635
Melting point=140-142° C.

EXAMPLE 2

3-cyano-N-[(2S)-2-(3,4-dichlorophenyl)-4-{4-[(1R, 2S)-1-(2-furyl)-2,3-dihydroxy-propyl]-piperazin-1-yl}butyl]-N-methyl-1-naphthamide (process 2)

A) 23.0 g of tert. butoxycarbonyl-piperazine (formula X) were dissolved in 600 ml ethanol under nitrogen at 30° C. 25 g of 2-furanboronic acid (formula VIII) and 22.0 g of 80% pure (D)-glyceraldehyde (formula IX) in 400 ml ethanol were heated to reflux for 7 hours. The mixture was cooled down to room temperature and concentrated to dryness. The residue was dissolved in 200 ml ethyl acetate and 50 ml methyl-tert.-butylether and successively washed with a solution of 20 g of KOH in 200 ml water. The residue was further washed with six portions of 150 ml water before drying over sodium sulfate. After evaporation of the solvent, 54.7 g of 4-((2S)-1-furan-2-yl-2-hydroxy-propyl)-piperazine-1-carboxylic acid tert-butyl ester (formula XI) was obtained.

$[\alpha]_D^{20}$=+34.6° (c=1, methanol).

Melting point: 92 to 93° C.

B) 16.3 g of 4-((2S)1-furan-2-yl-2-hydroxy-propyl)-piperazine-1-carboxylic acid tert-butyl ester (formula XI, from reaction step A)) were dissolved in 50 ml methyl-tert.-butylether under stirring. 160 ml of 5 N HCl were added to give a solution and a strong gas evolution. After stirring for 24 hours, the solution was poured in 200 ml methyl-tert.-butylether and further stirred. A solid precipitate which was filtered and washed with 20 ml of methyl-tert.-butylether. After drying under vacuum at 60° C. 13.5 g of (2S)-1-furan-2-yl-1-piperazin-1-yl-butan-2-ol dihydrochloride (formula XII) were isolated.

Specific rotation: +14.0° (c=1, methanol).

C) 28.4 g of sodium hydrogen carbonate in 150 ml water were added to a suspension of 25 g of 2S-(3,4-Dichloro-phenyl)-4-methylamino-butan-1-ol (formula IV) hydrochloride in 500 ml of THF under stirring. A solution of 21.1 g of tertiary butyloxycarbonyl anhydride in 200 ml THF was added and the combined reaction mixture was stirred for four hours. The THF was distilled off under vacuum and 500 ml of ethyl acetate was added to the residue. 100 ml of a saturated solution of sodium hydroxyl carbonate was added, followed by the addition of 300 ml water. The organic phase was removed and dried over sodium sulfate. The organic solvent was removed to leave an oily material which was purified by column chromatography on Silica gel to give 29.5 g of [(2S)-2-(3,4-dichloro-phenyl)-4-hydroxy-butyl]-methyl-carbamic acid tert-butyl ester (formula XX) as a colorless oily pure material which slowly crystallizes. 20 g of [(2S)-2-(3,4-dichloro-phenyl)-4-hydroxy-butyl]-methyl-carbamic acid tert-butyl ester (formula XX) were dissolved under stirring in 150 ml of dichloromethane at room temperature under nitrogen to which 6 ml of triethylamine and 3 ml methanesulfonyl chloride were added dropwise. The solution was stirred for three days at room temperature and finally concentrated. 200 ml of ethyl acetate and toluene were added and the organic layer was washed with 100 ml water, with a saturated solution of sodium hydrogen carbonate until pH 8 to 9 was reached and finally washed with 100 ml water. The organic phase was dried over sodium sulfate and evaporated to dryness to give 13.3 g of the corresponding mesylate (formula XXI). 13.3 g of the mesylate were dissolved under stirring in 200 ml of acetone at room temperature under nitrogen and 22 g of sodium iodide were added. The mixture was stirred until completion of the reaction (three days). Acetone was distilled off, and 200 ml ethyl acetate were added as well as 33 g of sodium thiosulfate pentahydrate dissolved in 200 ml water. The aqueous phase was then separated, and the organic phase was successively washed with 100 ml of an saturated solution of sodium hydrogen carbonate followed by three times with 100 ml of water. The organic phase was dried over sodium sulfate and concentrated to dryness to give 15.1 g of [(2S)-2-(3,4-dichloro-phenyl)-4-iodo-butyl]-methyl-carbamic acid tert-butyl ester (formula XIII).

D) A 10 ml solution of 200 mg of [(2S)-2-(3,4-dichloro-phenyl)-4-iodo-butyl]-methyl-carbamic acid tert-butyl ester (formula XIII, from reaction step C)) in 10 ml THF were added to a suspension of 450 mg of (2S)-1-furan-2-yl-1-piperazin-1-yl-butan-2-ol dihydrochloride (formula XIII, from reactions step B)) and 1 ml of triethylamine in 50 ml THF under stirring at room temperature. About 100 mg of $Na_2CO_3$ were added and the mixture was boiled to reflux for 15 hours. After cooling to room temperature, the suspension was concentrated in vacuum and the residue was dissolved in 50 ml of ethyl acetate and 200 mg of KOH in 10 ml of water. The organic phase was washed 4 times with 20 ml of water, dried on sodium sulfate and evaporated to dryness to deliver 203 mg of a yellowish compound identified in LC-MS as the expected amine XIV.

E) 3 ml of HCl (5N) in isopropanol were added to 460 mg of the amine XIV from reaction step D) dissolved at 30° C. in 2 ml methylene chloride under stirring at room temperature. After 1 hour, a precipitate appeared and 50 ml of methyl-tert.-butylether were added and the mixture was stirred for 15 hours. The white solid was isolated by filtration, washed 3 times with 10 ml methyl-tert.-butylether and dried in vacuum at 80° C. The remaining amount of methyl-tert.-butylether was eliminated by dissolving the compound in methanol and distilling off the solvents to deliver 407 mg (yield: 85%) of a foam used without further purification.

F) A suspension of 168 mg 3-cyano-naphthalene-1-carbonyl chloride (formula III, from reaction step A) of process 1) in 20 ml of methylene chloride were added dropwise to 367 mg of the amine from reaction step E) dissolved in 10 ml of THF, 10 ml of water and 200 mg of KOH. After stirring for 15 hour at room temperature, the reaction mixture was concentrated in vacuum and redissolved in a mixture of 30 ml of ethyl acetate and 30 ml methyl-tert.-butylether. The organic phase was washed 4 times with 20 ml of water, dried on sodium sulfate and concentrated to dryness under vacuum to deliver 420 mg of 3-cyano-N-[(2S)-2-(3,4-dichlorophenyl)-4-{4-[(1R,2S)-1-(2-furyl)-2,3-dihydroxypropyl]-pipera-zin-1-yl}butyl]-N-methyl-1-naphthamide (formula I) identified in LC-MS and NMR.

$[\alpha]_D^{20}$=−27.6° (c=1, methanol).

MS-data (ES+): M+ bei m/z=635

Melting point=140-142° C.

EXAMPLE 3

3-cyano-N-[(2S)-2-(3,4-dichlorophenyl)-4-{4-[(1R,2S)-1-(2-furyl)-2,3-dihydroxy-propyl]-piperazin-1-yl}butyl]-N-methyl-1-naphthamide (modified process 2)

A) 12.2 g DMSO in 100 ml dichloromethane are added dropwise to 7.3 g oxalyl chloride in 100 ml dichloromethane under nitrogen at −70° C. with stirring. The resulting mixture was stirred for another 15 minutes before 20 g of [2S-(3,4-dichloro-phenyl)-4-hydroxy-butyl]-methyl-carbamic acid tert-butyl ester in 200 ml dichloromethane were added. The mixture was stirred at −70° C. for one hour before 40.3 ml of triethylamine in 50 ml dichloromethane were added dropwise. The solution was stirred at −70° C. for 15 minutes and then allowed to warm up to room temperature. The solvent was removed and the residue was dissolved in 300 ml of toluene and 200 ml of ethyl acetate. The resulting solution was washed six times with 200 ml of a saturated solution of NaCl in water, dried over sodium sulfate and concentrated to dryness to deliver 19.7 g of [(2S)-2-(3,4-dichloro-phenyl)-4-oxo-butyl]-methyl-carbamic acid tert-butyl ester aldehyde (formula XVI).

B) A mixture of 300 mg of (2S)-1-furan-2-yl-1-piperazin-1-yl-butan-2-ol dihydrochloride (formula XII, from reaction step B) of Process 2), 200 mg of sodium acetate in 50 ml THF and 100 µl of acetic acid were added to a suspension of 280 mg of [(2S)-2-(3,4-dichloro-phenyl)-4-oxo-butyl]-methyl-carbamic acid tert-butyl ester aldehyde (formula XVI, from reaction step A)) in 20 ml THF. The resulting mixture was stirred for 5 hours at room temperature. Subsequently, 240 mg of sodium triacetoxyborohydride were added and the suspension was stirred for 15 hours at room temperature. The suspension was then concentrated in vacuum, and the residue was dissolved in 30 ml of ethyl acetate, 30 ml of methyl-tert.-butylether and 600 mg of KOH in water. The organic phase was washed 4 times with 20 ml of water. The organic solvents were dried over sodium sulfate and distilled off to give 463 mg of a glassy compound used without further purification in accordance with process steps E) and F) of process 2.

EXAMPLE 4

3-cyano-N-[(2S)-2-(3,4-dichlorophenyl)-4-{4-[(1R,2S)-1-(2-furyl)-2,3-dihydroxy-propyl]-piperazin-1-yl}butyl]-N-methyl-1-naphthamide (process 3)

A) 58.0 g 3-cyano-naphthalene-1-carboxylic acid (formula II) was suspended in 600 ml of dichloromethane. 2 ml of DMF were added successively under stirring. To this initial suspension, 35 ml of oxalyl dichloride in 65 ml dichloromethane were added slowly. The mixture was stirred for 4 hours at 30° C. to 40° C. The obtained solution was concentrated to dryness and 67 g of 3-cyano-naphthalene-1-carbonyl chloride (formula III) was isolated, stored in a refrigerator and used without further purification.

B) 20 g of 3S-(3,4-dichlorophenyl)-4-methylaminobutan-1-ol (formula IV) were suspended in 200 ml of THF under stirring at room temperature. 12 g of KOH dissolved in 100 ml of water were added leading to a solution. 17.2 g of 3-cyano-naphthalene-1-carbonyl chloride (formula III, from reaction step A) were added and stirred for 3 hours. The organic solvents were eliminated and the remaining mixture was supplemented with ethyl acetate and methyl-tert.-butylether. The water phase was eliminated while the organic phase was washed four times with 50 ml of water and dried over sodium sulfate. The organic phase was concentrated to dryness, providing 31.8 g of a yellowish solid (3-cyano-naphthalene-1-carboxylic acid [2S-(3,4-dichloro-phenyl)-4-hydroxy-butyl]-methyl-amide; formula V) which was used without further purification.

C) 25 ml DMSO in 100 ml dichloromethane are added dropwise to 9.7 g oxalyl chloride in 100 ml dichloromethane under nitrogen at −70° C. under stirring. The resulting was stirred for another 15 minutes before 31.7 g of (3-cyano-naphthalene-1-carboxylic acid [2S-(3,4-dichlorophenyl)-4-hydroxybutyl]-methyl-amide (formula V, from reaction step B) in 200 ml dichloromethane and 6 ml DMSO were added. The mixture was stirred for another hour at −70° C. 52 ml of triethylamine in 50 ml dichloromethane were added dropwise. The solution was stirred at −70° C. for 15 minutes and then allowed to warm up to room temperature. The solvent was removed and the residue was dissolved in 300 ml of toluene and 200 ml of ethyl acetate. The resulting solution was washed six times with 200 ml of a saturated solution of NaCl in water, dried over sodium sulfate and concentrated to dryness to give 31.0 g of [7-cyanonaphthalene-2-carboxylic acid [(2S)-2-(3,4-dichlorophenyl)-4-oxo-butyl]-methyl-amide (formula XVII).

D) 860 mg of (2S)-1-furan-2-yl-1-piperazin-1-yl-butan-2-ol dihydrochloride (formula XII, from reaction step B) of Process 2), 860 mg of [7-cyanonaphthalene-2-carboxylic acid [(2S)-2-(3,4-dichlorophenyl)-4-oxo-butyl]-methyl-amide (formula XVII, from reaction step C)), 200 µl acetic acid and 0.1 ml water were suspended in 150 ml THF and stirred for four hours. 1.49 g sodium triacetoxyborohydride were added and the reaction mixture was stirred for 15 hours at room temperature. The solution was concentrated and 0.4 g KOH in 1 ml water as well as 10 ml methyl-tert.-butylether and 50 ml ethyl acetate were added. Water was eliminated and the organic phase was washed four times with 20 ml water, dried over sodium sulfate and concentrated to dryness to give 1.32 g of a foam. This foam was dissolved in 9 ml isopropyl alcohol and heated to 60° C. A product crystallized which was re-dissolved by adding 28 ml isopropyl alcohol (added in three portions) at 75° C. After cooling down to room temperature, crystals were obtained which were washed three times with 20 ml methyl-tert.-butylether to yield 1.15 g 3-cyano-N-[(2S)-2-(3,4-dichlorophenyl)-4-{4-[(1R,2S)-1-(2-furyl)-2,3-dihydroxypropyl]piperazin-1-yl}butyl]-N-methyl-1-naphthamide monoisopropylate (formula I).

Melting point: 165-166° C.

EXAMPLE 5

3-cyano-N-[(2S)-2-(3,4-dichlorophenyl)-4-{4-[(1R,2S)-1-(2-furyl)-2-oxo[1,3]-dioxolan-4-yl]piperazin-1-yl}methyl]-N-methyl-1-naphthamide

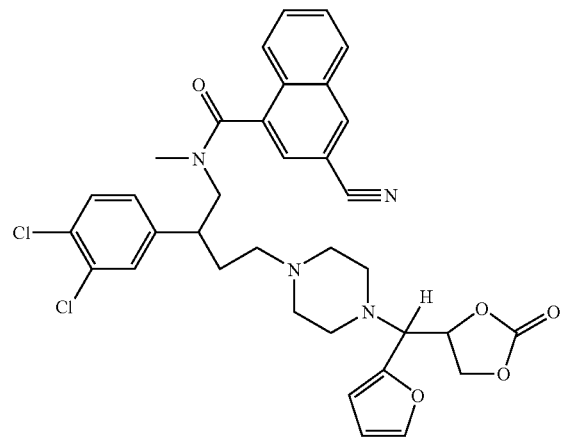

650 mg of 3-cyano-N-[(2S)-2-(3,4-dichlorophenyl)-4-{4-[(1R,2S)-1-(2-furyl)-2,3-dihydroxy-propyl]piperazin-1-yl}butyl]-N-methyl-1-naphthamide from any of the above processes were suspended in 50 ml dichloromethane at room temperature. 216 mg of N,N'-carbonydiimidazole in 60 ml dichloromethane were added over a period of 70 minutes. The solution was stirred for 5 hours at room temperature before being washed with 50 ml of a saturated solution of sodium hydrogen carbonate. The mixture was then washed with water until a pH of 6 was reached. Removal of the solvents in vacuum lead to 634 mg of 3-cyano-N-[(2S)-2-(3,4-dichlorophenyl)-4-{4-[(1R,2S)-1-(2-furyl)-2-oxo[1,3]dioxo-lan-4-yl]piperazin-1-yl}methyl]-N-methyl-1-naphthamide.

EXAMPLE 6

3-cyano-N-[(2S)-2-(3,4-dichlorophenyl)-4-{4-[(1R,2S)-1-(2-furyl)-2-oxo[1,3]-dioxolan-4-yl]piperazin-1-yl}methyl]-N-methyl-1-naphthamide monoacetate 350 mg of 3-cyano-N-[(2S)-2-(3,4-dichlorophenyl)-4-{4-[(1R,2S)-1-(2-furyl)-2-oxo[1,3]dioxolan-4-yl]piperazin-1-yl}methyl]-N-methyl-1-naphthamide monoethanolate were dissolved in 50 ml ethyl acetate at room temperature under stirring. 120 µl of acetyl chloride and 250 µl of triethylamine were added successively. The reaction mixture was stirred further for 3 hours at room temperature and washed with 50 ml of a saturated solution of sodium carbonate in water and five times with 30 ml of water. After drying with sodium sulfate, the solution was concentrated to dryness to give 342 mg of a mixture which contains mainly monoacetic ester of the primary alcohol as seen in LC-MS and NMR. The mixture was purified by column chromatography on 10 g of $SiO_2$ with ethyl acetate/ethanol as mixture of eluents to give 136 mg of the monoacetate which was characterized by LC/MS and NMR.

EXAMPLE 7

3-cyano-N-[(2S)-2-(3,4-dichlorophenyl)-4-{4-[(1R,2S)-1-(2-furyl)-2-oxo[1,3]-dioxolan-4-yl]piperazin-1-yl}methyl]-N-methyl-1-naphthamide monoacetate 230 mg of 3-cyano-N-[(2S)-2-(3,4-dichlorophenyl)-4-{4-[(1R,2S)-1-(2-furyl)-2-oxo-[1,3]di-oxolan-4-yl]piperazin-1-yl}methyl]-N-methyl-1-naphthamide monoethanolate were dissolved in 10 ml of pyridine at room temperature. 150 µl of acetyl chloride in 10 ml of methylene chloride were added dropwise. The reaction mixture was stirred for 4 hours at room temperature and after addition of 10 ml of water, concentrated in vacuum. The residue was dissolved in 50 ml ethyl acetate and was washed 6 times with 20 ml water. LC-MS and NMR show the presence of diacetate as the main compound in the raw mixture. 150 mg of the mixture were fractionated by column chromatography on 10 g of $SiO_2$ to yield 84 mg of the expected diester as confirmed by NMR and MS.

The compounds of formula I listed in the following Table 8 below may be prepared according to the process described in the above examples or according to processes analogous thereto.

TABLE 8

Examples of compounds of formula I.

| Structure | $R^1$ | $R^2$ | $R^3$ | $R^4$ | $R^5$ | $R^7$ | $R^8$ | $R^9$ | $R^{10}$ | $R^{11}$ | k | l | m | n |
|---|---|---|---|---|---|---|---|---|---|---|---|---|---|---|
| 1 | $CH_3$ | Cl | Cl | 2-furanyl | H | H | — | — | — | H | 1 | 0 | 0 | 0 |
| 2 | $CH_3$ | Cl | Cl | 2-furanyl | H | H | H | H | — | H | 1 | 1 | 1 | 0 |
| 3 | $CH_3$ | Cl | Cl | 2-furanyl | H | H | H | H | — | H | 1 | 1 | 1 | 0 |
| 4 | $CH_3$ | Cl | Cl | 3-thiophen | H | H | H | — | H | H | 1 | 1 | 0 | 1 |
| 5 | $CH_3$ | Cl | Cl | 3-thiophen | H | H | H | — | H | H | 1 | 1 | 0 | 1 |
| 6 | $CH_3$ | Cl | Cl | 2-furanyl | $CH_2OH$ from $R^6$ | — | — | — | — | H | 0 | 0 | 0 | 0 |
| 7 | $CH_3$ | Cl | Cl | 2-furanyl | H | H | H | H | — | H | 1 | 1 | 0 | 0 |
| 8 | $CH_3$ | Cl | Cl | 3-thiophen | H | H | — | — | — | H | 1 | 0 | 0 | 0 |
| 9 | $CH_3$ | Cl | Cl | 2-thiophen | H | H | — | — | — | H | 1 | 0 | 0 | 0 |
| 10 | $CH_3$ | Cl | Cl | 3-thiophen | H | 5-ring carbonyl | | | | — | — | — | — | — |
| 11 | $CH_3$ | Cl | Cl | 2-furanyl | H | 5-ring carbonyl | | | | — | — | — | — | — |
| 12 | $CH_3$ | Cl | Cl | 3-furanyl | H | H | — | — | — | H | 1 | 0 | 0 | 0 |
| 13 | $CH_3$ | Cl | Cl | 2-furanyl | 5-ring methylene | | | | | — | — | — | — | — |
| 14 | $CH_3$ | Cl | Cl | 2-furanyl | | H | — | — | — | H | 1 | 0 | 0 | 0 |
| 15 | $CH_3$ | Cl | Cl | 4-methyl-phenyl | H | H | — | — | — | H | 1 | 0 | 0 | 0 |
| 16 | $CH_3$ | Cl | Cl | 4-methoxy-phenyl | H | H | — | — | — | H | 1 | 0 | 0 | 0 |
| 17 | $CH_3$ | Cl | Cl | 2-benzo[b]furan | H | H | — | — | — | H | 1 | 0 | 0 | 0 |
| 18 | $CH_3$ | Cl | Cl | 5-chloro-2-thiophene | H | H | — | — | — | H | 1 | 0 | 0 | 0 |
| 19 | $CH_3$ | Cl | Cl | 2-methoxy-phenyl | H | H | — | — | — | H | 1 | 0 | 0 | 0 |
| 20 | $CH_3$ | Cl | Cl | 3-pyridine | H | H | — | — | — | H | 1 | 0 | 0 | 0 |
| 21 | $CH_3$ | Cl | Cl | 3,4-methylene-dioxyphenyl | H | H | — | — | — | H | 1 | 0 | 0 | 0 |
| 22 | $CH_3$ | Cl | Cl | 2-benzo[b]thiophene | H | H | — | — | — | H | 1 | 0 | 0 | 0 |
| 23 | $CH_3$ | Cl | Cl | phenyl | H | H | — | — | — | H | 1 | 0 | 0 | 0 |
| 24 | $CH_3$ | Cl | Cl | benzyl | H | H | — | — | — | H | 1 | 0 | 0 | 0 |
| 25 | $CH_3$ | Cl | Cl | 2-furanyl | H | — | — | — | — | H | 0 | 0 | 0 | 0 |
| 26 | $CH_3$ | Cl | Cl | benzyl | H | H | — | — | — | $COCH_3$ | 1 | 0 | 0 | 0 |
| 27 | $CH_3$ | Cl | Cl | 2-furanyl | H | $COCH_3$ | — | — | — | $COCH_3$ | 0 | 0 | 0 | 0 |
| 28 | $CH_3$ | Cl | Cl | 2-furanyl | H | — | — | — | — | H | 0 | 0 | 0 | 0 |

The compounds of Examples 15 to 22 listed in table 8 above were also prepared using an automated preparation process. For this, per batch in each case 200 µl of a 0.25 N aqueous stock solution of the corresponding carbohydrate compound of formula IX was measured in a microreaction vessel and evaporated in a vacuum to largely remove the water. The residue was taken up in 200 µl ethanol. In each case 200 µl of a 0.25 mol/l ethanolic stock solution of racemic or enantiomerically pure (cf. in each case the corresponding particulars in table 7) N-[(2S)-2-(3,4-dichlorophenyl)-4-(1-piperazinyl)butyl]-N-methylbenzamide of formula VII and 200 μl of a 0.25 N ethanolic stock solution of the corresponding boronic acid (=dihydroxyborane compound) of formula VIII was added to this initial solution. The reaction mixture was first heated to 80° C. for 2 h and then cooled to room temperature and 1 ml ethanol was added thereto. Then 100 mg basic Amberjet® ion exchange resin was added and the reaction vessel was shaken for 2 h. The ion exchanger was filtered out, was subsequently washed twice with 500 μl ethanol each time and the solvent was evaporated to dryness in a vacuum. Samples of the residue in each case were taken without further purification for high-performance liquid chromatography (=HPLC) and for automatic mass spectroscopy to determine the purity and to confirm the structure.

EXAMPLE 8

Capsules containing 3-cyano-N-[(2S)-2-(3,4-dichlorophenyl)-4-{4-[(1R,2S)-1-(2-furyl)-2,3-dihydroxypropyl]piperazin-1-yl}butyl]-N-methyl-1-naphthamide Capsules having the following composition per capsule were produced:

| | |
|---|---|
| 3-cyano-N-[(2S)-2-(3,4-dichlorophenyl)-4-{4-[(1R,2S)-1-(2-furyl)-2,3-dihydroxypropyl]piperazin-1-yl}butyl]-N-methyl-1-naphthamide | 20 mg |
| Corn starch | 60 mg |
| Lactose | 300 mg |
| Ethyl acetate | q.s. |

The active substance, the corn starch and the lactose were processed into a homogenous pasty mixture using EE. The paste was ground, and the resulting granules were placed on a suitable tray and dried at 45° C. in order to remove the solvent. The dried granules were passed through a crusher and mixed in a mixer with the further following auxiliaries:

| | |
|---|---|
| Talcum | 5 mg |
| Magnesium stearate | 5 mg |
| Corn starch | 9 mg |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A compound corresponding to formula I:

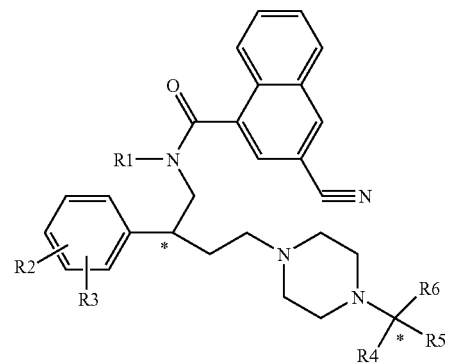

wherein
R1 is selected from the group consisting of hydrogen and $C_1$ to $C_4$ alkyl;
R2 is halogen;
R3 is halogen;
R4 is selected from the group consisting of 2-furanyl, 3-furanyl, 2-thiophene, 3-thiophene, phenyl, benzyl, 2-benzofuranyl, 3-benzofuranyl, 5-chloro-2-thiophene, 4-methylphenyl, 3,4-methylenedioxyphenyl, 2-methoxyphenyl, 4-methoxyphenyl, 2-pyridinyl, 3-pyridinyl, 1-benzo[c]thiophene, 4-benzo[c]thiophene, 5-benzo[c]thiophene, 2-benzo[b]thiophene, 3-benzo[b]thiophene, 4-benzo[b]thiophene, 5-benzo[b]thiophene, 6-benzo[b]thiophene, 7-benzo[b]thiophene, 1-benzo[1,3]dioxole, 4-benzo[1,3]dioxole, and 5-benzo[1,3]dioxole;
R5 is selected from the group consisting of hydrogen or R6;
R6 represents a subgroup of the formula

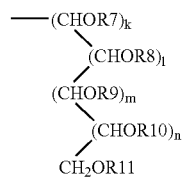

wherein
R7 is selected from the group consisting of hydrogen or $C_1$ to $C_4$ alkanoyl, or together with another substituent, selected from the group consisting of R8, R9, R10 and R11, may form a 5- or 6-ring bridged by carbonyl, or by methylene optionally substituted by $C_1$ to $C_4$ alkyl or $C_4$ to $C_5$ alkylene;
R8 is selected from the group consisting of hydrogen or $C_1$ to $C_4$ alkanoyl, or together with another substituent, selected from the group consisting of R7, R9, R10 and R11, may form a 5- or 6-ring bridged by carbonyl, or by methylene optionally substituted by $C_1$ to $C_4$ alkyl or $C_4$ to $C_5$alkylene;
R9 is selected from the group consisting of hydrogen or $C_1$ to $C_4$ alkanoyl, or together with another substituent, selected from the group consisting of R7, R8, R10 and R11, may form a 5- or 6-ring bridged by carbonyl, or by methylene optionally substituted by $C_1$ to $C_4$ alkyl or $C_4$ to $C_5$ alkylene;

R10 is selected from the group consisting of hydrogen or $C_1$ to $C_4$ alkanoyl, or together with another substituent, selected from the group consisting of R7, R8, R9 and R11, may form a 5- or 6-ring bridged by carbonyl, or by methylene optionally substituted by $C_1$ to $C_4$ alkyl or $C_4$ to $C_5$ alkylene;

R11 is selected from the group consisting of hydrogen and $C_1$ to $C_4$ alkanoyl, or together with R7, R8, R9 or R10 forms a 5- or 6-member ring bridged by carbonyl or by methylene optionally substituted by $C_1$ to $C_4$ alkyl or $C_4$ to $C_5$ alkylene;

k is 0 or 1;
l is 0 or 1;
m is 0 or 1, and
n is 0 or 1;
or a physiologically compatible acid addition salt thereof.

2. A compound according to claim 1, wherein R1 represents methyl.

3. A compound according to claim 1, wherein R2 and R3 each represent chlorine.

4. A compound according to claim 1, wherein R4 is selected from the group consisting of 2-furanyl, 3-furanyl, 2-thiophene, 3-thiophene, phenyl, benzyl, 2-benzofuranyl, 5-chloro-2-thiophene, 4-methylphenyl, 3,4-methylenedioxyphenyl, 2-methoxyphenyl and 4-methoxyphenyl.

5. A compound according to claim 4 wherein R4 is selected from the group consisting of 2-furanyl, 3-furanyl, 2-thiophene, and 3-thiophene.

6. A compound according to claim 1, wherein R5 represents hydrogen.

7. A compound according to claim 1, wherein R7 and R11 each represent hydrogen; k is 1; and l, m and n are each zero.

8. A compound according to claim 1, wherein R7, R8 and R11 each represent hydrogen; k and l are each 1; and m and n are each zero.

9. A compound according to claim 1, wherein R7, R8, R9 and R11 are each hydrogen; R10 is hydrogen or $C_1$ to $C_4$ alkanoyl, k, l and m are each 1; and n is zero.

10. A compound according to claim 1, wherein R7 to R11 are each hydrogen; k, l and m are each 1; and n is zero.

11. A compound according to claim 1, wherein the chiral center *C to which the phenyl ring carrying the substituent groups R2 and R3 is bonded in formula I is in the S configuration.

12. A compound according to claim 1, selected from the group consisting of:

3-cyano-N-[(2S)-2-(3,4-dichlorophenyl)-4-{4-[(1R,2S)-1-(2-furyl)-2,3-dihydroxypropyl]piperazin-1-yl}butyl]-N-methyl-1-naphthamide;

(2S,3R)-2-(acetyloxy)-3-{4-[(3S)-4-[3-cyano-1-naphthoyl)(methyl)amino]-3-(3,4-dichlorophenyl)butyl]piperazin-1-yl}-3-(2-furyl)propyl acetate;

3-cyano-N-[(2S)-2-(3,4-dichlorophenyl)-4-{4-[1-(2-furyl)-2-hydroxyethyl]piperazin-1-yl}butyl]-N-methyl-1-naphthamide;

3-cyano-N-[(2S)-2-(3,4-dichlorophenyl)-4-{4-[(1R,2S,3R,4R)-1-(2-furyl)-2,3,4,5-tetrahydroxypentyl]piperazin-1-yl}butyl]-N-methyl-1-naphthamide;

3-cyano-N-[(2S)-2-(3,4-dichlorophenyl)-4-{4-[(1R,2S,3S,4R)-1-(2-furyl)-2,3,4,5-tetrahydroxypentyl]piperazin-1-yl}butyl]-N-methyl-1-naphthamide;

3-cyano-N-[(2S)-2-(3,4-dichlorophenyl)-4-{4-[(1S,2S,3S,4R)-2,3,4,5-tetrahydroxy-1-(3-thienyl)pentyl]piperazin-1-yl}butyl]-N-methyl-1-naphthamide;

3-cyano-N-[(2S)-2-(3,4-dichlorophenyl)-4-{4-[(1S,2S,3R,4R)-2,3,4,5-tetrahydroxy-1-(3-thienyl)pentyl]piperazin-1-yl}butyl]-N-methyl-1-naphthamide;

3-cyano-N-[(2S)-2-(3,4-dichlorophenyl)-4-{4-[1-(2-furyl)-2-hydroxy-1-(hydroxymethyl)ethyl]piperazin-1-yl}butyl]-N-methyl-1-naphthamide;

3-cyano-N-[(2S)-2-(3,4-dichlorophenyl)-4-{4-[1-(2-furyl)-2-hydroxy-1-(hydroxymethyl)ethyl]piperazin-1-yl}butyl]-N-methyl-1-naphthamide;

3-cyano-N-[(2S)-2-(3,4-dichlorophenyl)-4-{4-[(1S,2S)-2,3-dihydroxy-1-(3-thienyl)propyl]piperazin-1-yl}butyl]-N-methyl-1-naphthamide;

3-cyano-N-[(2S)-2-(3,4-dichlorophenyl)-4-{4-[(1R,2S)-2,3-dihydroxy-1-(2-thienyl)propyl]piperazin-1-yl}butyl]-N-methyl-1-naphthamide;

3-cyano-N-[(2S)-2-(3,4-dichlorophenyl)-4-{4-[(S)-[(4S)-2-oxo-1,3-dioxolan-4-yl](3-thienyl)methyl]piperazin-1-yl}butyl]-N-methyl-1-naphthamide;

3-cyano-N-[(2S)-2-(3,4-dichlorophenyl)-4-(4-{(R)-2-furyl[(4S)-2-oxo-1,3-dioxolan-4-yl]methyl}piperazin-1-yl)butyl]-N-methyl-1-naphthamide;

3-cyano-N-[(2S)-2-(3,4-dichlorophenyl)-4-{4-[(1S,2S)-1-(3-furyl)-2,3-dihydroxypropyl]piperazin-1-yl}butyl]-N-methyl-1-naphthamide;

3-cyano-N-[(2S)-2-(3,4-dichlorophenyl)-4-{4-[1-(2-furyl)-2,3-dihydroxypropyl]piperazin-1-yl}butyl]-N-methyl-1-naphthamide;

3-cyano-N-[(2S)-2-(3,4-dichlorophenyl)-4-{4-[(1S,2S)-2,3-dihydroxy-1-phenylpropyl]piperazin-1-yl}butyl]-N-methyl-1-naphthamide;

3-cyano-N-[(2)-2-(3,4-dichlorophenyl)-4-{4-[(1S,2S)-2,3-dihydroxy-1-(4-methoxyphenyl)propyl]piperazin-1-yl}butyl]-N-methyl-1-naphthamide;

N-[(2S)-4-{4-[(1R,2S)-1-(1-benzofuran-2-yl)-2,3-dihydroxypropyl]piperazin-1-yl}-2-(3,4-dichlorophenyl)butyl]-3-cyano-N-methyl-1-naphthamide;

N-[(2S)-4-{4-[(1R,2S)-1-(5-chloro-2-thienyl)-2,3-dihydroxypropyl]piperazin-1-yl}-2-(3,4-dichlorophenyl)butyl]-3-cyano-N-methyl-1-naphthamide;

N-[(2S)-4-{4-[(1S,2S)-1-(1,3-benzodioxol-5-yl)-2,3-dihydroxypropyl]piperazin-1-yl}-2-(3,4-dichlorophenyl)butyl]-3-cyano-N-methyl-1-naphthamide; and N-[(2S)-4-{4-[(1R,2S)-1-(1-benzothien-2-yl)-2,3-dihydroxypropyl]piperazin-1-yl}-2-(3,4-dichlorophenyl)butyl]-3-cyano-N-methyl-1-naphthamide.

13. A pharmaceutical composition comprising a compound according to claim 1 and at least one pharmaceutical carrier or excipient.

14. A process for preparing a compound according to claim 1, said process comprising:

(a) reacting a compound of formula VII wherein R1, R2 and R3 have the meanings given in claim 1, with a compound of formula VIII,

R4-B(OH)$_2$     VIII wherein R4 has the meaning given in claim 1, and with a compound of formula IX,

IX wherein R5 and R6 have the meanings given in claim 1, to yield a compound of formula I; or (b) reacting a compound of formula XV,

XV wherein R1, R2, R3, R4, R5 and R6 have the meanings given above,
with a compound of formula III

III to yield a compound of formula I; or (c) reacting a compound of formula XVII

XVII wherein R1, R2 and R3 have the meanings given above,
with a compound of formula XII

XII wherein R4, R5 and R6 have the meanings given above,
to yield a compound of formula I; and
optionally converting the compound of formula I into a corresponding, physiologically compatible acid addition salt.

15. A compound corresponding to formula VII:

VII wherein
R1 is selected from the group consisting of hydrogen and $C_1$ to $C_4$ alkyl;
R2 is halogen, and
R3 is halogen.

16. A compound according to claim 15, wherein R1 represents methyl, and R2 and R3 each represent chlorine.

* * * * *